(12) United States Patent
Pavani

(10) Patent No.: US 9,250,187 B1
(45) Date of Patent: Feb. 2, 2016

(54) LABELED WAFER INSPECTION

(71) Applicant: Sri Rama Prasanna Pavani, Palo Alto, CA (US)

(72) Inventor: Sri Rama Prasanna Pavani, Palo Alto, CA (US)

(73) Assignee: Exnodes Inc., Palo Alto, CA (US)

( * ) Notice: Subject to any disclaimer, the term of this patent is extended or adjusted under 35 U.S.C. 154(b) by 0 days.

(21) Appl. No.: 14/537,922

(22) Filed: Nov. 11, 2014

(51) Int. Cl.
*F21V 9/16* (2006.01)
*G01J 1/58* (2006.01)
*G01N 21/64* (2006.01)
*G01N 21/95* (2006.01)

(52) U.S. Cl.
CPC .......... *G01N 21/643* (2013.01); *G01N 21/6456* (2013.01); *G01N 21/9501* (2013.01); *G01N 2021/646* (2013.01); *G01N 2021/6439* (2013.01)

(58) Field of Classification Search
CPC ....... G01N 21/91; G01N 21/64; G01N 23/00; G01N 21/9501; G01N 21/94
USPC ...................................................... 250/459.1
See application file for complete search history.

(56) References Cited

U.S. PATENT DOCUMENTS

| | | | |
|---|---|---|---|
| 2,920,203 A | 1/1960 | Switzer | |
| 3,490,873 A | 1/1970 | Corl | |
| 4,744,833 A * | 5/1988 | Cooper | ..................... B08B 6/00 134/1 |
| 7,323,681 B1 * | 1/2008 | Oldham | ............. G01N 21/6428 250/208.1 |
| 8,304,242 B2 | 11/2012 | Zhang | |
| 8,357,536 B2 | 1/2013 | Wuister | |
| 2006/0244957 A1 * | 11/2006 | Furman | ............. G01N 21/8806 356/237.4 |
| 2007/0105394 A1 * | 5/2007 | Bauer | ..................... H01L 21/56 438/758 |
| 2010/0278400 A1 * | 11/2010 | Piestun | .............. G01N 21/6456 382/128 |
| 2011/0129930 A1 * | 6/2011 | Wuister | .................. G01N 21/91 436/35 |
| 2011/0266460 A1 * | 11/2011 | Martinelli | .......... G01N 21/6454 250/459.1 |

* cited by examiner

*Primary Examiner* — David Porta
*Assistant Examiner* — Meenakshi Sahu

(57) ABSTRACT

A system and method for detecting a feature located on a surface, comprising: attaching a label to said feature; generating a label radiation from said label, a feature radiation from said feature, and a surface radiation from said surface; collecting said label radiation, said feature radiation, and said surface radiation; separating said label radiation from said feature radiation and said surface radiation; capturing the separated label radiation for generating an image of label, with said image of label having one or more pixels; and locating label pixels corresponding to said label radiation by searching for pixels, in said image of label, that possess substantially different pixel values when compared to other pixels in local neighborhood, whereby said feature is located by detecting said label.

20 Claims, 11 Drawing Sheets

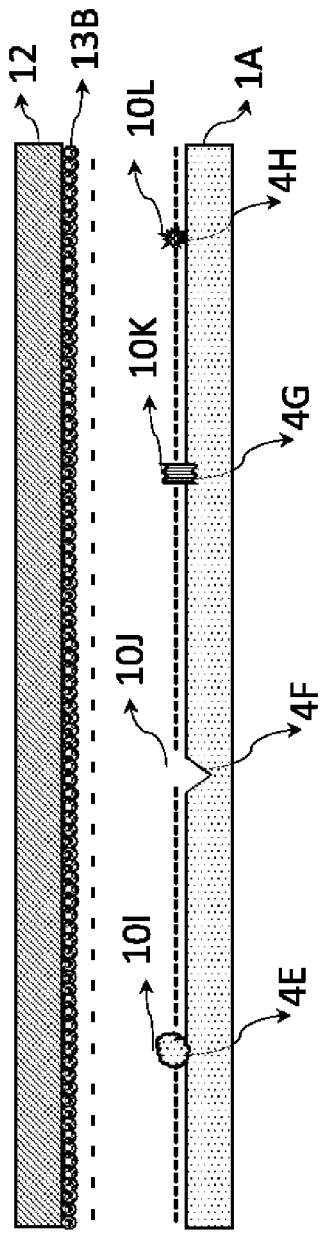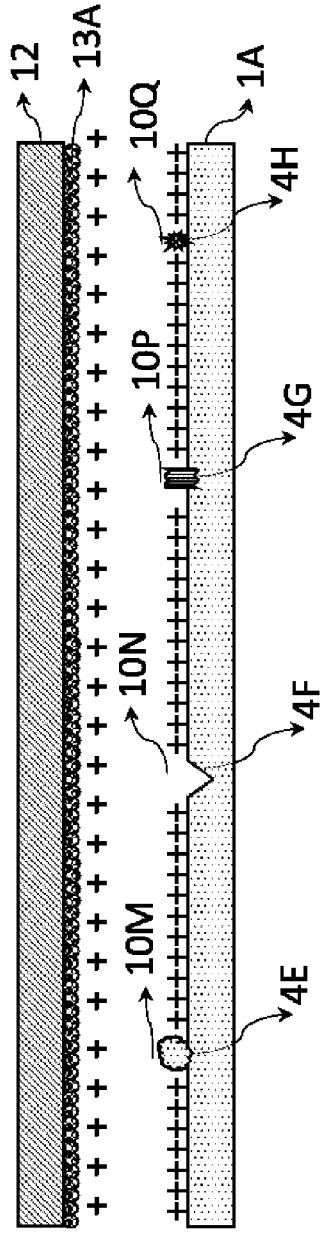
FIG. 3C
FIG. 3D

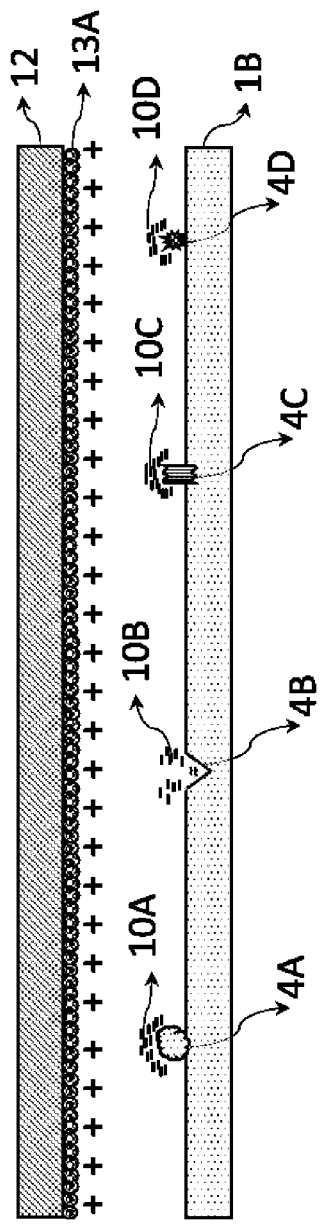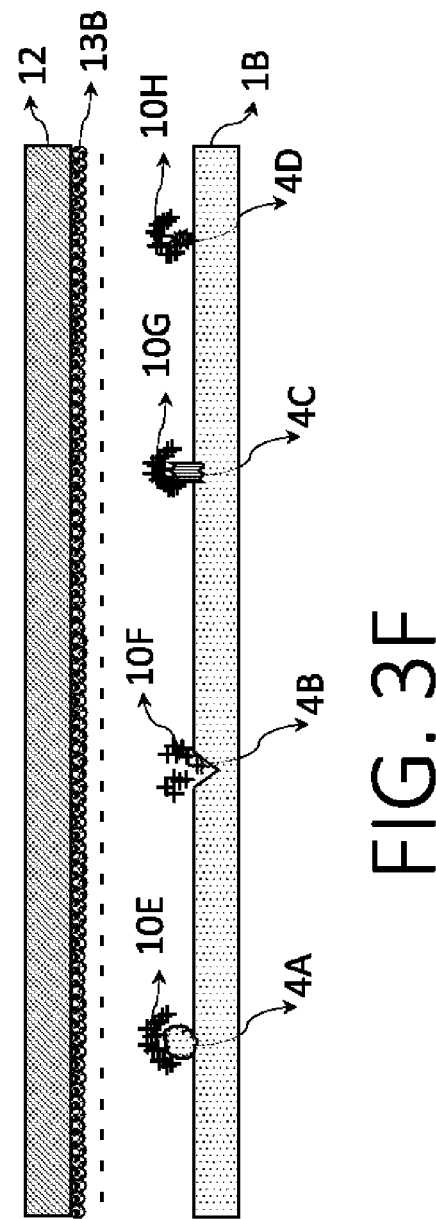
FIG. 3E
FIG. 3F

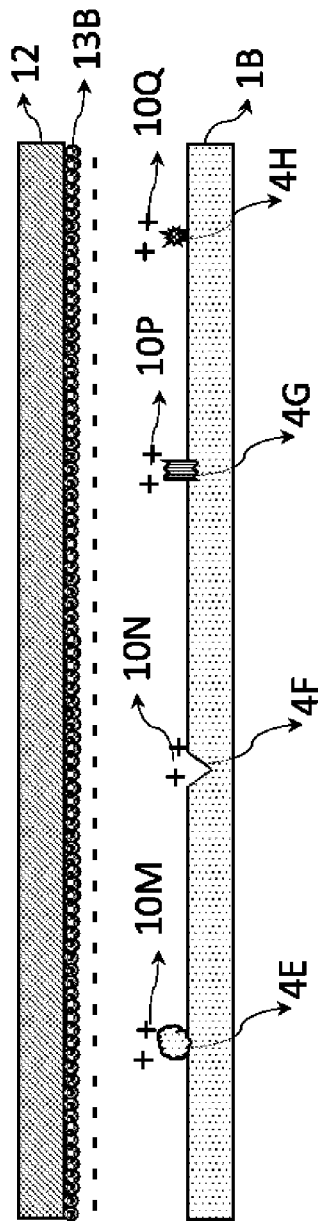
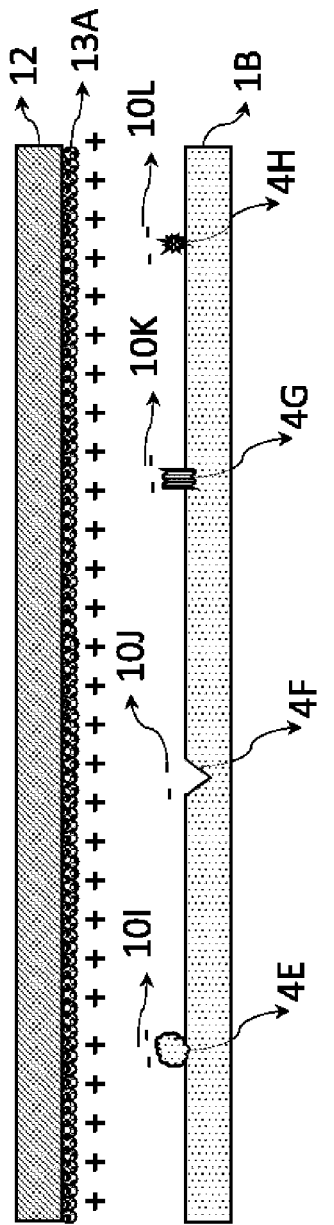

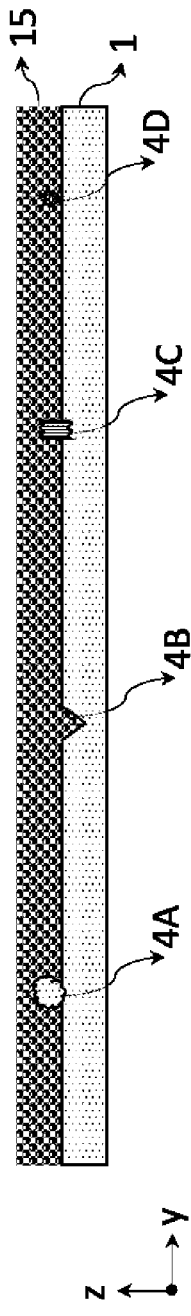
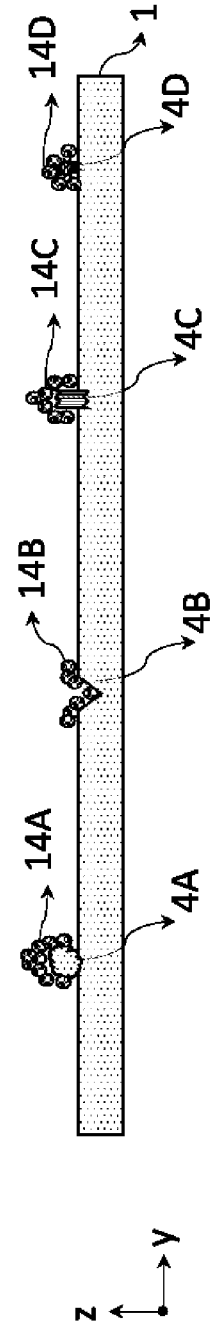

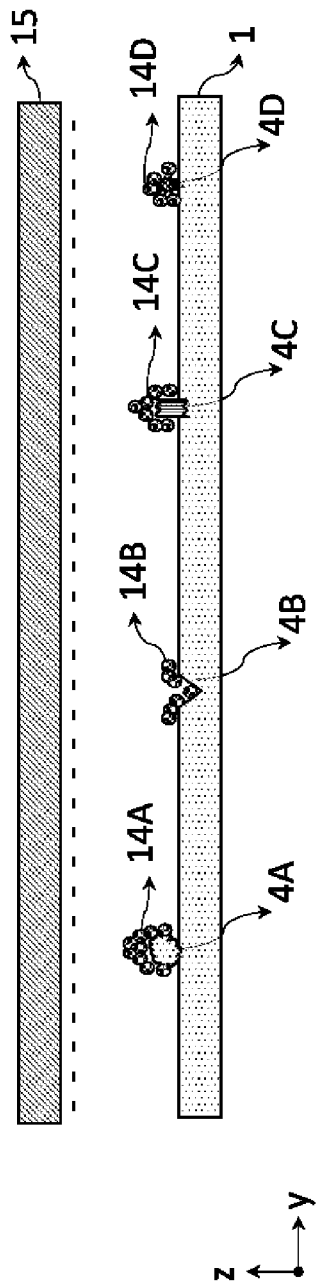
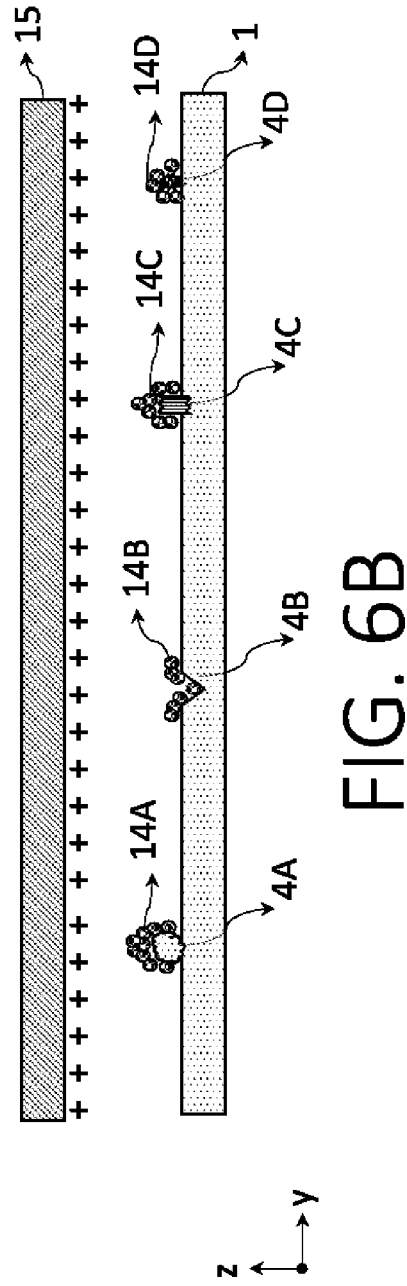

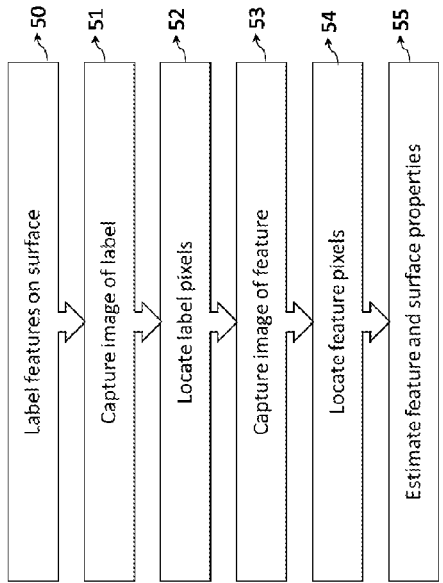
FIG. 10
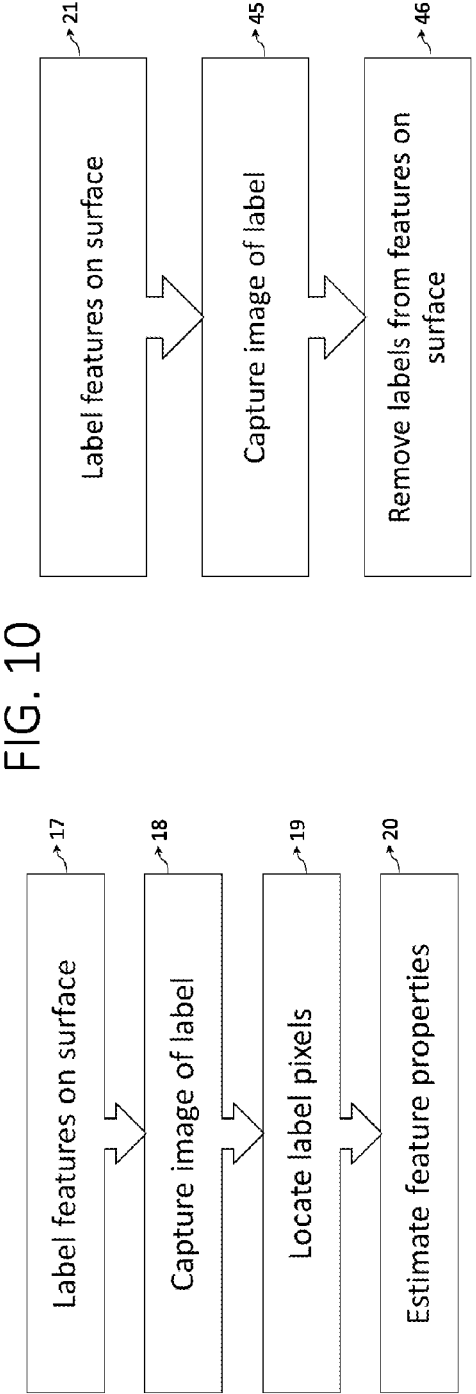
FIG. 11
FIG. 9

LABELED WAFER INSPECTION

FIELD OF THE INVENTION

This invention relates generally to wafer inspection and more particularly to labeling of features on a wafer for improved wafer inspection.

BACKGROUND

Integrated circuit (IC) technology has continually advanced in the last few decades. In doing so, ICs have enabled a variety of applications ranging from smart consumer electronic devices to interplanetary communication. Interestingly, advances in ICs have also resulted in a dramatic reduction in cost of individual IC components. This reduction in cost is enabled by the ability of modern IC fabrication technology to produce increasingly large number of IC components on a single semiconductor wafer.

A couple of factors play an indispensable role in setting the trend of continuous IC advancements. Firstly, in what is known as node scaling, the size of the components of ICs are shrinking with each next generation technology node. This means that an increasingly large number of components can be fabricated on a single wafer. Remarkably, the shrinking of components also enable a significant increase in IC performance. Secondly, the size of semiconductor wafers continually increase to accommodate an increasingly more number of components on a single wafer. Together, the two factors allowed IC components to be mass produced at increasingly large scales.

Although modern semiconductor fabrication has enabled mass production of ICs, the produced ICs are useful only if they are functional. The ratio of the number of ICs that meet performance specifications to the total number of produced ICs is called yield, an important quantity that semiconductor fabs strive to maximize. Yield maximization leads to reduction in unit cost of IC. However, maximizing yield is a formidable task because of the exhaustive number and complexity of process steps involved in IC fabrication. The fabrication of ICs typically involves hundreds of process steps where a semiconductor wafer is subjected to steps such as ion implantation, deposition, lithography, etching, and polishing. Together, these steps fabricate intricate nanometer scale structures in ICs. Because of the exhaustive nature of IC fabrication, it is difficult to use data from functional tests of ICs to associate a failure in IC functionality to an abnormality in a particular process step. Nevertheless, knowing precisely where the abnormality occurred is crucial for maximizing yield. Accordingly, wafer inspection tools are employed after every significant process step to inspect for the presence of abnormalities or defects. If an increased number of defects are observed at a particular stage of fabrication, efforts are undertaken to identify the root cause of defects and to eliminate the root cause. Containing the root cause of defects quickly would prevent defects from affecting multiple wafers, thereby minimizing the impact on yield. Therefore, yield maximization is dependent on: a) ability of wafer inspection tools to detect defects, and b) effectively eliminating the source of defects.

Unfortunately, advances in semiconductor fabrication have made it very difficult to maximize yield. This is primarily because of the inability of wafer inspection tools to detect increasingly small yield-affecting defects. As the size of structures in ICs shrink due to node scaling, increasingly small defect sizes become problematic. In other words, the probability of a 14 nm defect to affect yield is substantially higher in a 14 nm technology node than in a 22 nm node. In order to maintain yield in a next generation technology node, the defect sensitivity of wafer inspection tools must follow the node scaling factor of the next generation technology node. In other words, if a next generation technology node shrinks by a factor of 1.5× with respect to a previous generation technology node, defect sensitivity of wafer inspection tools will also need to shrink by 1.5× in order for the next generation node to maintain the same yield as the previous generation node. However, in hindsight, it is discomforting to notice that the defect sensitivity of wafer inspection tools have been significantly lagging behind node scaling. In the last ten years, while the smallest IC structures shrank from 130 nm to 14 nm (over 9× reduction), defect sensitivity improved at a substantially slower rate from 50 nm to 20 nm (2.5× reduction). For the 130 nm technology node, defect sizes 2.6× smaller than the node size were detected. However, for the 14 nm technology node, wafer inspection tools are unable to even detect defects sizes 1× the node size. As a result, an increasing number of yield affecting defects pass undetected through wafer detection systems, leading to a significant negative impact in yield.

There are two fundamental reasons for the inability of wafer inspection tools to match up to the fast pace of node scaling. Firstly, the intensity of light scattered by defects decreases exponentially as the size of defect decreases. A 2× reduction in defect size leads to a 64× reduction in scattered light intensity. As a result, photodetectors used in wafer inspection tools receive exponentially smaller radiation levels from small defect sizes. Secondly, surface roughness present in wafer creates an undesirable background radiation called haze, which overwhelms scattered radiation from small defects. Traditional wafer inspection tools strive to maximize defect sensitivity by reducing the wavelength of incident light and increasing the power of incident light. However, doing so not only increases scattered radiation from defects but also increases haze. Furthermore, higher power beams with shorter wavelengths have the potential to induce a permanent damage to a semiconductor wafer.

Traditional wafer inspection suffers from a number of problems: a) reduced sensitivity; b) reduced scattering intensity for small defects; c) background scatting due to surface roughness; d) low signal to background ratios; e) need for a high power laser beam; and f) need for increasingly short wavelength laser beams.

Accordingly, there is a need for an improved wafer inspection that can improve sensitivity; increase scattering intensity for small defects; reduce background scattering due to surface roughness; increase signal to background ratios; relax the need for a high power laser beam; and relax the need for shorter wavelength laser beams.

SUMMARY

The invention is a system and method for detecting a feature located on a surface by detecting a label attached to the feature.

In some embodiments, the invention is a system for detecting a feature located on a surface, comprising: a label attached to said feature; an electromagnetic radiation incident on said label, said feature, and said surface to generate a label radiation from said label, a feature radiation from said feature, and a surface radiation from said surface; an imaging module positioned to collect said label radiation, said feature radiation, and said surface radiation; a filter positioned to receive radiation from said imaging module, wherein said filter separates said label radiation from said feature radiation and said surface radiation; a detector having one or more pixels disposed to capture the separated label radiation for generating an image of label; and a processor configured to locate label pixels corresponding to said label radiation by searching for pixels, in said image of label, that possess substantially different pixel values when compared to other pixels in local neighborhood, whereby said feature is located by detecting said label.

In some embodiments, the invention is a method for detecting a feature located on a surface, comprising: attaching a label to said feature; generating a label radiation from said label, a feature radiation from said feature, and a surface radiation from said surface; collecting said label radiation, said feature radiation, and said surface radiation; separating said label radiation from said feature radiation and said surface radiation; capturing the separated label radiation for generating an image of label, with said image of label having one or more pixels; and locating label pixels corresponding to said label radiation by searching for pixels, in said image of label, that possess substantially different pixel values when compared to other pixels in local neighborhood, whereby said feature is located by detecting said label.

BRIEF DESCRIPTION OF THE DRAWINGS

FIG. 3C illustrates a method to attach a negatively charged label to a non-conducting feature on a conducting surface using electrostatic force, in accordance with the invention.

FIG. 3D illustrates a method to attach a positively charged label to a non-conducting feature on a conducting surface using electrostatic force, in accordance with the invention.

FIG. 3E illustrates a method to attach a positively charged label to a conducting feature on a non-conducting surface using electrostatic force, in accordance with the invention.

FIG. 3F illustrates a method to attach a negatively charged label to a conducting feature on a non-conducting surface using electrostatic force, in accordance with the invention.

FIG. 3G illustrates a method to attach a negatively charged label to a non-conducting feature on a non-conducting surface using electrostatic force, in accordance with the invention.

FIG. 3H illustrates a method to attach a positively charged label to a non-conducting feature on a non-conducting surface using electrostatic force, in accordance with the invention.

FIG. 4 illustrates a method to attach a label to a feature on a surface by immersing the surface in a medium comprising the label, in accordance with the invention.

FIG. 5 illustrates a surface having labeled features, in accordance with the invention.

FIG. 6A illustrates a method to detach a label from a feature on a surface using a negatively charged substrate, in accordance with the invention.

FIG. 6B illustrates a method to detach a label from a feature on a surface using a positively charged substrate, in accordance with the invention.

FIG. 9 shows an exemplary flowchart to estimate feature properties using an image of label, in accordance with the invention.

FIG. 10 shows an exemplary flowchart to estimate feature properties using an image of label and an image of feature, in accordance with the invention.

FIG. 11 shows an exemplary flowchart to attach and detach labels from features on surface, in accordance with the invention.

DETAILED DESCRIPTION OF THE PREFERRED EMBODIMENTS

Figure 1:
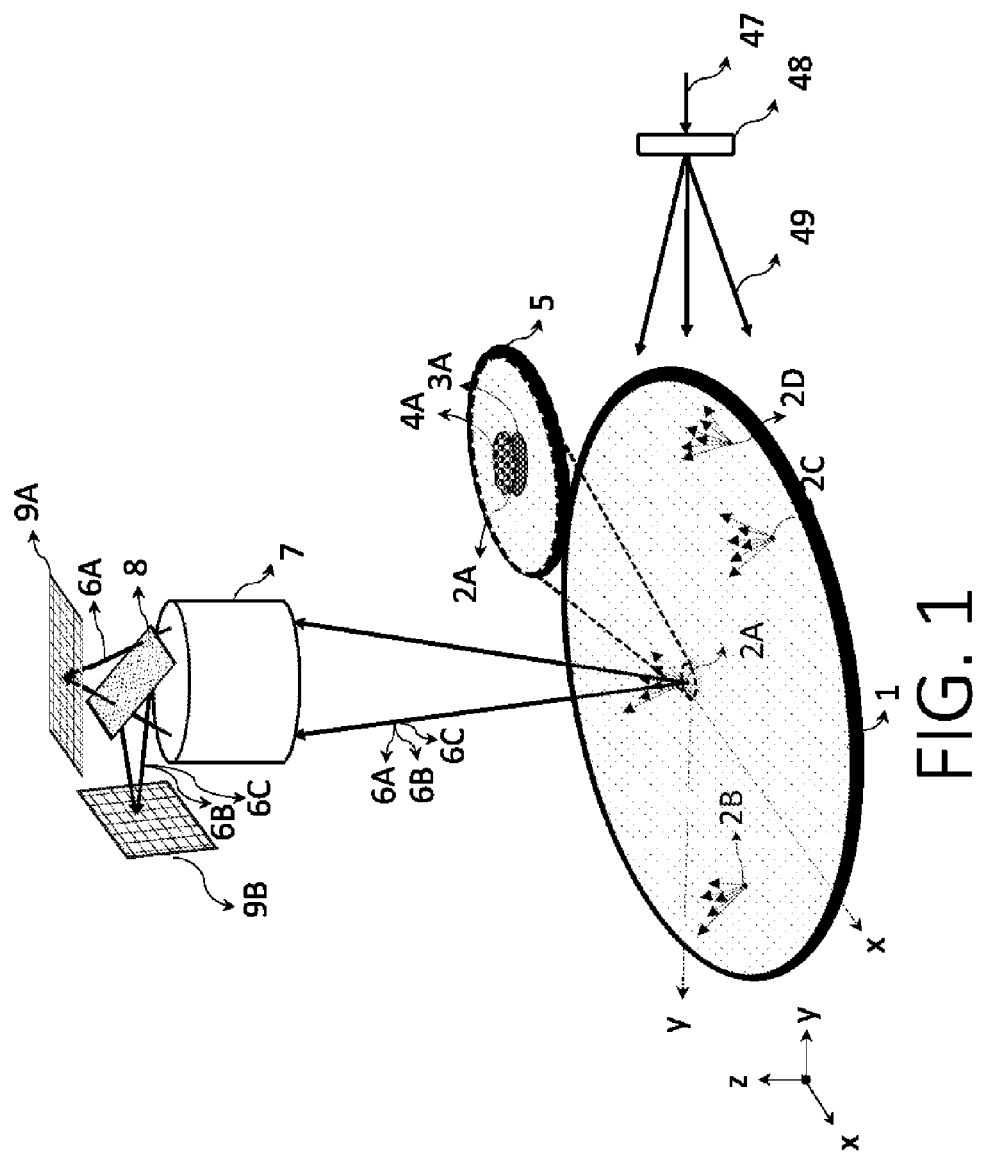
FIG. 1 shows a labeled wafer inspection system with a detector for detecting label radiation, and another detector for detecting feature radiation and surface radiation, in accordance with the invention.

FIG. 1 shows a labeled wafer inspection system with a detector for detecting label radiation, and another detector for detecting feature radiation and surface radiation, in accordance with the invention. An electromagnetic beam 47 is incident on a beam shaper 48 to generate a shaped beam 49. The shaped beam is incident on surface 1 to illuminate a predetermined region of surface 1. Surface 1 comprises an area to be inspected by the wafer inspection system. In some embodiments, surface 1 is a semiconductor wafer such as a Silicon wafer. In other embodiments, surface 1 is a glass wafer. In some embodiments, the shaped beam illuminates a substantial area of surface 1. In such embodiments, beam shaper 48 expands the electromagnetic beam 47. In other embodiments, the shaped beam 49 illuminates a spot on surface 1. In such embodiments, beam shaper 48 shapes the electromagnetic beam 47 to illuminate a predetermined spot size and shape on surface 1. Surface 1 comprises four labeled features, 2A, 2B, 2C, and 2D, which are illuminated by the shaped beam 49. A close up 5 of labeled feature 2A shows a feature 3A and a label 4A. Label 4A is attached to feature 3A. In some embodiments, label 4A is attached to feature 3A with an electrostatic force. In other embodiments, label 4A is attached to feature 3A with a chemical bond. Similarly, labeled features, 2B, 2C, and 2D, also comprise labels attached to features. Features include abnormalities or defects and other structures present on surface 1. Abnormalities or defects include particles, process induced defects, crystal originated pits, residues, scratches, and bumps.

When the shaped beam 49 is incident on surface 1, a majority of the photons in the beam undergo specular reflection if surface 1 is smooth. In practice, most surfaces exhibit at least an atomic scale roughness. Surface roughness refers to minute deviations in the height of a surface from an average height value. Surface roughness causes a fraction of incident beam 49 to be scattered. This scattered radiation from surface roughness is called as haze or surface radiation 6C.

On the other hand, when shaped beam 49 is incident on a labeled feature, two types of radiation are generated. Firstly, the shaped beam 49 is scattered by the feature. This scattering by feature generates a feature radiation 6B. Secondly, the shaped beam 49 interacts with the label. This interaction with label generates a label radiation 6A. The label radiation 6A has a substantially different wavelength than surface radiation 6C and feature radiation 6B. In some embodiments, label radiation 6A has a longer wavelength than surface radiation 6C and feature radiation 6B. In other embodiments, label radiation 6A has a shorter wavelength than surface radiation 6C and feature radiation 6B. In some embodiments, surface radiation 6C and feature radiation 6B have substantially similar wavelengths.

In some embodiments, label 4A is a fluorescent marker. In other embodiments, label 4A is a phosphorescent marker. In some embodiments, the label absorbs radiation from shaped beam 49 and emits a label radiation having a longer wavelength than feature radiation 6B and surface radiation 6C. In other embodiments, the label absorbs two or more photons of shaped beam 49 simultaneously, and emits a label radiation 6A having a shorter wavelength than feature radiation 6B and surface radiation 6C.

An imaging module 7 collects label radiation 6A, surface radiation 6C, and feature radiation 6B. The collected radiation is incident on a filter 8 to separate label radiation 6A from surface radiation 6C and feature radiation 6B. In some embodiments, filter 8 is a dichroic beam splitter or a dichroic mirror that transmits label radiation 6A, but reflects surface radiation 6C and feature radiation 6B. The transmission band of the filter 8 is designed to transmit label radiation 6A with minimal attenuation. Further, the reflection band of the filter 8 is designed to reflect feature radiation 6B and surface radiation 6C with minimal attenuation.

The label radiation 6A transmitted from filter 8 is detected by a detector 9A having one or more photodetector elements called pixels. In some embodiments, detector 9A is an image sensor. In other embodiments, detector 9A is a photomultiplier tube or a photodiode. In some embodiments, detector 9A is of complementary metal oxide semiconductor type image sensor. In other embodiments, detector 9A is of charged coupled device type image sensor.

The feature radiation 6B and surface radiation 6C reflected from filter 8 is detected by a detector 9B having one or more photodetector elements called pixels. In some embodiments, detector 9B is an image sensor. In other embodiments, detector 9B is a photomultiplier tube or a photodiode. In some embodiments, detector 9B is of complementary metal oxide semiconductor type image sensor. In other embodiments, detector 9B is of charged coupled device type image sensor. In some embodiments, a spatial filter is positioned between filter 8 and detector 9B, wherein the spatial filter modulates feature radiation and surface radiation in order to maximize feature sensitivity.

Images are captured from image sensors 9A and 9B. In some embodiments where surface radiation 6C has a large magnitude, the image captured from image sensor 9A exhibits a higher contrast than the image captured from image sensor 9B. Contrast of an image refers to the ratio of the difference of the largest and smallest pixel values to the sum of the largest and smallest pixel values. The largest and smallest pixel values are obtained from a local neighborhood of pixels. The reason for the higher contrast of image captured from image sensor 9A is because of the lack of presence of surface radiation 6C. Accordingly, the signal to background ratio of images acquired from image sensor 9A is higher than the signal to background ratio of images acquired from image sensor 9B. Signal to background ratio is defined as the ratio of peak signal pixel value to average background pixel value. In the case of an image captured from image sensor 9A, signal to background refers to the ratio of a peak pixel value corresponding to label radiation to an average pixel value in the local neighborhood of the peak pixel value. In the case of an image captured from image sensor 9B, signal to background refers to the ratio of a peak pixel value corresponding to feature radiation to an average pixel value in the local neighborhood of the peak pixel value corresponding to surface radiation.

An image of label is captured from image sensor 9A. Label pixels are located in image of label by searching for pixels whose values are substantially different from other pixels in the local neighborhood. Similarly, an image of feature is captured from image sensor 9B. Feature pixels are located in image of feature by searching for pixels whose values are substantially different from other pixels in the local neighborhood. In some embodiments, information obtained from label pixels are combined with information obtained from feature pixels to estimate feature properties. Feature properties include the position and shape of features.

In some embodiments, image sensor 9A comprises a micro-optic sensor layer for detecting the phase of label radiation. By detecting the phase of label radiation, focused and defocused images of label are generated by computationally propagating the electromagnetic field incident on image sensor 9A. In some embodiments, image sensor 9B comprises a micro-optic sensor layer for detecting the phase of radiation incident on image sensor 9B. By detecting the phase of radiation, focused and defocused images of feature are generated by computationally propagating the electromagnetic field incident on image sensor 9B.

In some embodiments, at least two images are captured with at least two different optical path lengths between imaging module and image sensor. Phase is then estimated by using the transport of intensity equation. In some embodiments, the optical path length between an imaging module and an image sensor can be varied so that scattered radiation is detected at multiple values of optical path length. In some embodiments, optical path length between imaging module and image sensor may be varied by using a liquid crystal layer. In other embodiments, optical path length between image sensor and imaging module may be varied by inserting a uniform phase plate, such as a glass plate, between imaging module and image sensor. In some embodiments, optical path length between the image sensor and the imaging module may be varied by changing the distance between imaging module and image sensor using an actuator. In some embodiments, an iterative optimization algorithm may be used to estimate phase profile by starting with a random initial estimate for phase and arriving at a final estimate by propagating the electromagnetic field between two or more image planes separated by the optical path length.

In some embodiments, imaging module comprises a focus control. Focus control is tuned to generate a focused or defocused image of label and focused or defocused image of feature. In some embodiments, imaging module comprises a zoom control. Zoom control is tuned to vary the field of view and magnification of the imaging module. Accordingly, the area on surface 1 corresponding to image of label and image of feature can be varied. In some embodiments, imaging module comprises an aperture control. Aperture control is tuned to maximize collection of radiation while minimizing aberrations in the imaging module.

In some embodiments, labeled wafer inspection may be combined with dark-field wafer inspection by preventing the specular reflection of shaped beam 47 from being detected by detectors 9A and 9B.

Figure 2:
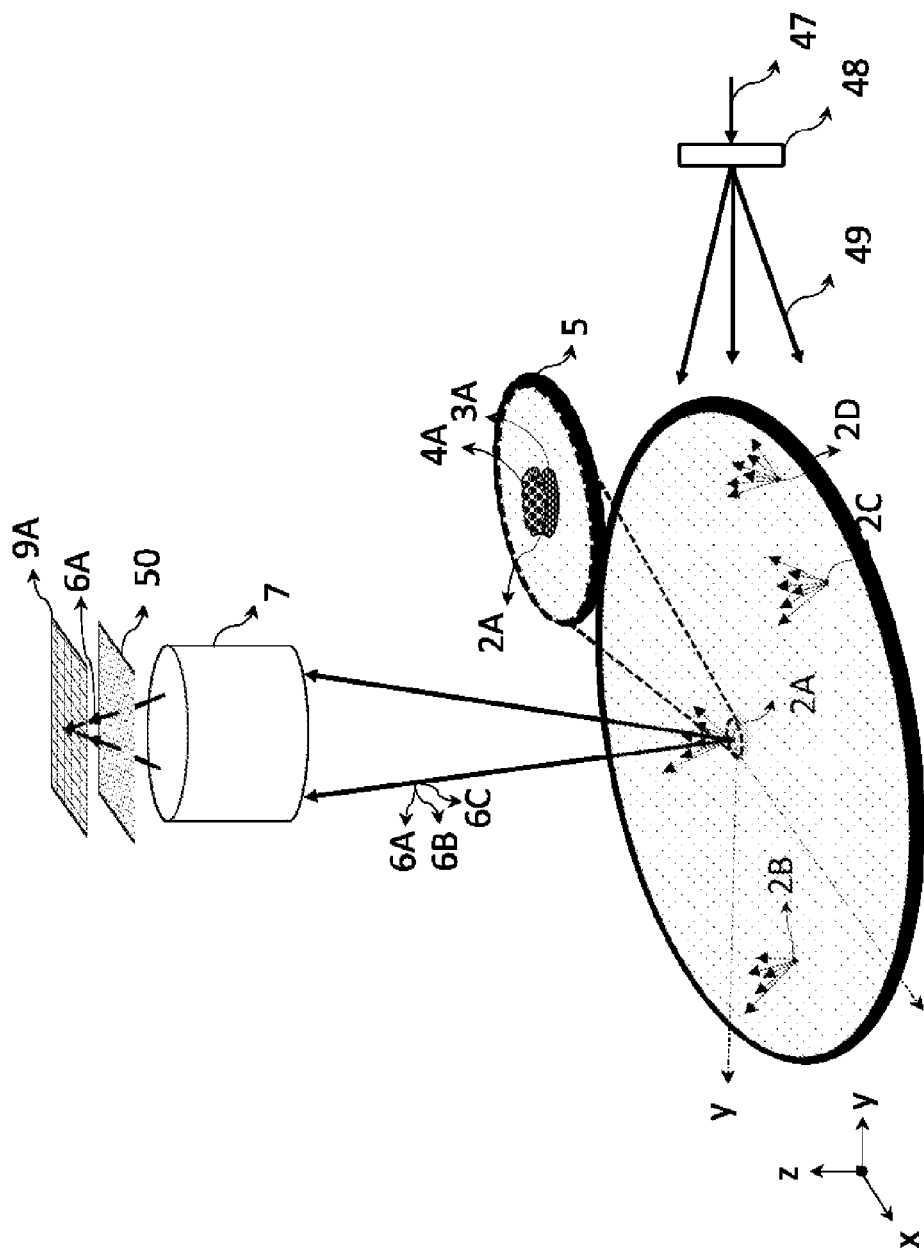
FIG. 2 shows a labeled wafer inspection system with a detector for detecting label radiation, in accordance with the invention.

FIG. 2 shows a labeled wafer inspection system with a detector for detecting label radiation, in accordance with the invention. An electromagnetic beam 47 is incident on a beam shaper 48 to generate a shaped beam 49. The shaped beam is incident on surface 1 to illuminate a predetermined region of surface 1. Surface 1 comprises an area to be inspected by the wafer inspection system. In some embodiments, surface 1 is a semiconductor wafer such as a Silicon wafer. In other embodiments, surface 1 is a glass wafer. In some embodiments, the shaped beam illuminates a substantial area of surface 1. In such embodiments, beam shaper 48 expands the electromagnetic beam 47. In other embodiments, shaped beam 49 illuminates a spot on surface 1. In such embodiments, beam shaper 48 shapes the electromagnetic beam 47 to illuminate a predetermined spot size and shape on surface 1. Surface 1 comprises four labeled features, 2A, 2B, 2C, and 2D, which are illuminated by the shaped beam 49. A close up 5 of labeled feature 2A shows a feature 3A and a label 4A. Label 4A is attached to feature 3A. In some embodiments, label 4A is attached to feature 3A with an electrostatic force. In other embodiments, label 4A is attached to feature 3A with a chemical bond. Similarly, labeled features, 2B, 2C, and 2D, also comprise labels attached to features. Features include abnormalities or defects and other structures present on surface 1. Abnormalities or defects include particles, process induced defects, crystal originated pits, residues, scratches, and bumps.

When the shaped beam 49 is incident on surface 1, a majority of the photons in the beam undergo specular reflection if surface 1 is smooth. In practice, most surfaces exhibit at least an atomic scale roughness. Surface roughness refers to minute deviations in the height of a surface from an average height value. Surface roughness causes a fraction of incident beam 49 to be scattered. This scattered radiation from surface roughness is called as haze or surface radiation 6C.

On the other hand, when shaped beam 49 is incident on a labeled feature, two types of radiation are generated. Firstly, the shaped beam 49 is scattered by the feature. This scattering by feature generates a feature radiation 6B. Secondly, the shaped beam 49 interacts with the label. This interaction with label generates a label radiation 6A. The label radiation 6A has a substantially different wavelength than surface radiation 6C and feature radiation 6B. In some embodiments, label radiation 6A has a longer wavelength than surface radiation 6C and feature radiation 6B. In other embodiments, label radiation 6A has a shorter wavelength than surface radiation 6C and feature radiation 6B. In some embodiments, surface radiation 6C and feature radiation 6B have substantially similar wavelengths.

In some embodiments, label 4A is a fluorescent marker. In other embodiments, label 4A is a phosphorescent marker. In some embodiments, the label absorbs radiation from shaped beam 49 and emits a label radiation having a longer wavelength than feature radiation 6B and surface radiation 6C. In other embodiments, the label absorbs two or more photons of shaped beam 49 simultaneously, and emits a label radiation 6A having a shorter wavelength than feature radiation 6B and surface radiation 6C.

An imaging module 7 collects label radiation 6A, surface radiation 6C, and feature radiation 6B. The collected radiation is incident on a filter 50 to separate label radiation 6A from surface radiation 6C and feature radiation 6B. In some embodiments, filter 8 is a dielectric interference filter that transmits label radiation 6A, but reflects surface radiation 6C and feature radiation 6B. In other embodiments, filter 50 is an absorptive filter that transmits label radiation 6A but absorbs surface radiation 6C and feature radiation 6B. The transmission band of the filter 50 is designed to transmit label radiation 6A with minimal attenuation. Further, the attenuation band of the filter 50 is designed to provide maximum attenuation so as to prevent feature radiation 6B and surface radiation 6C from passing through filter 50.

The label radiation 6A transmitted from filter 50 is detected by a detector 9A having one or more photodetector elements called pixels. In some embodiments, detector 9A is an image sensor. In other embodiments, detector 9A is a photomultiplier tube or a photodiode. In some embodiments, detector 9A is of complementary metal oxide semiconductor type image sensor. In other embodiments, detector 9A is of charged coupled device type image sensor.

Images are captured from image sensor 9A. In some embodiments where surface radiation 6C has a large magnitude, the image captured from image sensor 9A exhibits high contrast. Contrast of an image refers to the ratio of the difference of the largest and smallest pixel values to the sum of the largest and smallest pixel values. The largest and smallest pixel values are obtained from a local neighborhood of pixels. The reason for the high contrast of image captured from image sensor 9A is because of the lack of presence of surface radiation 6C. Accordingly, the signal to background ratio of images acquired from image sensor 9A is high. Signal to background ratio is defined as the ratio of peak signal pixel value to average background pixel value. In the case of an image captured from image sensor 9A, signal to background refers to the ratio of a peak pixel value corresponding to label radiation to an average pixel value in the local neighborhood of the peak pixel value.

An image of label is captured from image sensor 9A. Label pixels are located in image of label by searching for pixels whose values are substantially different from other pixels in the local neighborhood. Information obtained from label pixels are used to estimate feature properties. Feature properties include the position and shape of features.

In some embodiments, image sensor 9A comprises a micro-optic sensor layer for detecting the phase of label radiation. By detecting the phase of label radiation, focused and defocused images of label are generated by computationally propagating the electromagnetic field incident on image sensor 9A.

In some embodiments, at least two images are captured with at least two different optical path lengths between imaging module and image sensor. Phase is then estimated by using the transport of intensity equation. In some embodiments, the optical path length between an imaging module and an image sensor can be varied so that scattered radiation is detected at multiple values of optical path length. In some embodiments, optical path length between imaging module and image sensor may be varied by using a liquid crystal layer. In other embodiments, optical path length between image sensor and imaging module may be varied by inserting a uniform phase plate, such as a glass plate, between imaging module and image sensor. In some embodiments, optical path length between the image sensor and the imaging module may be varied by changing the distance between imaging module and image sensor using an actuator. In some embodiments, an iterative optimization algorithm may be used to estimate phase profile by starting with a random initial estimate for phase and arriving at a final estimate by propagating the electromagnetic field between two or more image planes separated by the optical path length.

In some embodiments, imaging module comprises a focus control. Focus control is tuned to generate a focused or defocused image of label. In some embodiments, imaging module comprises a zoom control. Zoom control is tuned to vary the field of view and magnification of the imaging module. Accordingly, the area on surface 1 corresponding to image of label can be varied. In some embodiments, imaging module comprises an aperture control. Aperture control is tuned to maximize collection of radiation while minimizing aberrations in the imaging module.

In some embodiments, labeled wafer inspection may be combined with dark-field wafer inspection by preventing the specular reflection of shaped beam 47 from being detected by detector 9A.

Figure 3A:
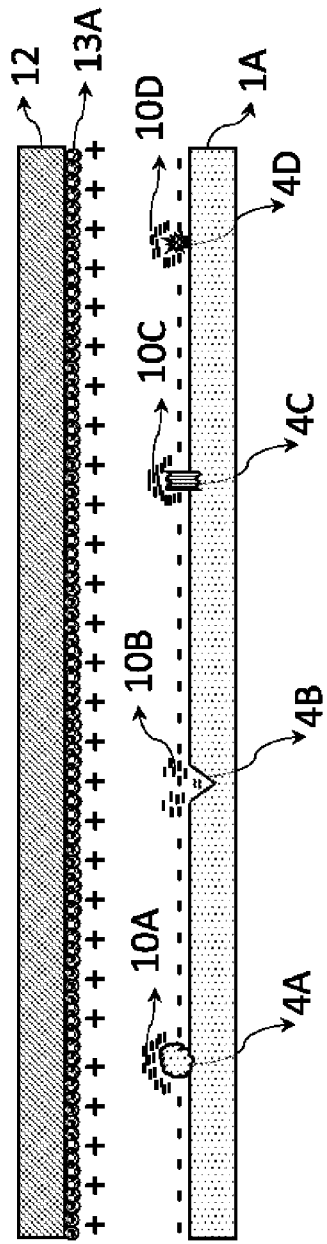
FIG. 3A illustrates a method to attach a positively charged label to a conducting feature on a conducting surface using electrostatic force, in accordance with the invention.

FIG. 3A illustrates a method to attach a positively charged label to a conducting feature on a conducting surface using electrostatic force, in accordance with the invention. A surface 1A comprises four conducting features, 4A, 4B, 4C, and 4D, having different shapes, sizes, and material properties. The surface 1A is negatively charged. In some embodiments, charging of surface 1A is by performed by electrical conduction. Electrical conduction involves bringing a charged conducting structure in contact with surface 1A. In other embodiments, charging of surface 1A is performed by electrostatic induction. Induction involves bringing a charged structure close to surface 1A, wherein the charged structure does not physically make contact with surface 1A. In some embodiments, charging of surface 1A is performed with friction, by physically interacting the surface with another material, so that surface 1A is negatively charged. Features, 4A, 4B, 4C, and 4D, are also negatively charged since they are also conductors. However, the density of charges on features, 4A, 4B, 4C, and 4D, is substantially higher than the density of charges on surface 1A. The distribution of charges 10A present on feature 4A is seen to be substantially denser than the distribution of charges on surface 1A. Similarly, the distribution of charges, 10B, 10C, and 10D, present on features, 4B, 4C, and 4D, is seen to be substantially denser than the distribution of charges on surface 1A. Charge density is proportional to the surface curvature. Since features, 4A, 4B, 4C, and 4D, have substantially higher curvature than surface 1A, charge density of the features are higher than that of the surface. A structure 12 comprising positively charged labels 13A is brought in proximity to surface 1A. The positively charged labels experience an electrostatic attractive force from the negatively charged features and the negatively charged surface. However, since the density of negative charges is higher on features than on surface, the electrostatic force between the labels and features is substantially higher than the electrostatic force between labels and surface. The electrostatic force between a label and a feature is directly proportional to the product of the charges in the label and the feature and inversely proportional to the square of the distance between the label and the feature. A predetermined distance between structure 12 and surface 1A allows one or more labels to experience an electrostatic force large enough to detach from structure 12 and attach to feature 4A. Similarly, other labels originally attached to structure 12 detach from structure 12 and attach features 4B, 4C, and 4D due to the electrostatic force between the label and the features. The electrostatic force between a label and a point on surface 1A is not large enough for the label to detach from structure 12. Accordingly, labels are attached only to features and not to surface 1A.

Figure 3B:
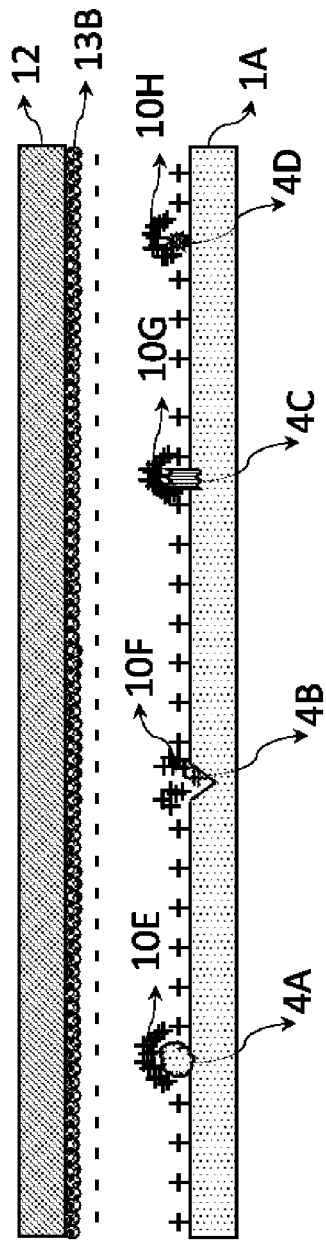
FIG. 3B illustrates a method to attach a negatively charged label to a conducting feature on a conducting surface using electrostatic force, in accordance with the invention.

FIG. 3B illustrates a method to attach a negatively charged label to a conducting feature on a conducting surface using electrostatic force, in accordance with the invention. A surface 1A comprises four conducting features, 4A, 4B, 4C, and 4D, having different shapes, sizes, and material properties. The surface 1A is positively charged. In some embodiments, charging of surface 1A is by performed by electrical conduction. Electrical conduction involves bringing a charged conducting structure in contact with surface 1A. In other embodiments, charging of surface 1A is performed by electrostatic induction. Induction involves bringing a charged structure close to surface 1A, wherein the charged structure does not physically make contact with surface 1A. In some embodiments, charging of surface 1A is performed with friction, by physically interacting the surface with another material, so that surface 1A is positively charged. Features, 4A, 4B, 4C, and 4D, are also positively charged since they are also conductors. However, the density of charges on features, 4A, 4B, 4C, and 4D, is substantially higher than the density of charges on surface 1A. The distribution of charges 10E present on feature 4A is seen to be substantially denser than the distribution of charges on surface 1A. Similarly, the distribution of charges, 10F, 10G, and 10H, present on features, 4B, 4C, and 4D, is seen to be substantially denser than the distribution of charges on surface 1A. Charge density is proportional to the surface curvature. Since features, 4A, 4B, 4C, and 4D, have substantially higher curvature than surface 1A, charge density of the features are higher than that of the surface. A structure 12 comprising negatively charged labels 13B is brought in proximity to surface 1A. The negatively charged labels experience an electrostatic attractive force from the positively charged features and the positively charged surface. However, since the density of positive charges is higher on features than on surface, the electrostatic force between the labels and features is substantially higher than the electrostatic force between labels and surface. The electrostatic force between a label and a feature is directly proportional to the product of the charges in the label and the feature and inversely proportional to the square of the distance between the label and the feature. A predetermined distance between structure 12 and surface 1A allows one or more labels to experience an electrostatic force large enough to detach from structure 12 and attach to feature 4A. Similarly, other labels originally attached to structure 12 detach from structure 12 and attach features 4B, 4C, and 4D due to the electrostatic force between the label and the features. The electrostatic force between a label and a point on surface 1A is not large enough for the label to detach from structure 12. Accordingly, labels are attached only to features and not to surface 1A.

FIG. 3C illustrates a method to attach a negatively charged label to a non-conducting feature on a conducting surface using electrostatic force, in accordance with the invention. A surface 1A comprises four non-conducting features, 4E, 4F, 4G, and 4H, having different shapes, sizes, and material properties. The surface 1A is negatively charged. In some embodiments, charging of surface 1A is by performed by electrical conduction. Electrical conduction involves bringing a charged conducting structure in contact with surface 1A. In other embodiments, charging of surface 1A is performed by electrostatic induction. Induction involves bringing a charged structure close to surface 1A, wherein the charged structure does not physically make contact with surface 1A. In some embodiments, charging of surface 1A is performed with friction, by physically interacting the surface with another material, so that surface 1A is negatively charged. Features, 4E, 4F, 4G, and 4H, are non-conducting, so they do not possess free electrons. Nevertheless, the electron clouds of atoms in the features are displaced when the features are charged. The charge density of negative charges on surface 1A is a lot higher when compared to charge density of negative charges on features 4E, 4F, 4G, and 4H. The distribution of charges on surface 1A is seen to be substantially denser than the distribution of charges 10I present on feature 4E. Similarly, the distribution of charges on surface 1A is substantially denser than the distribution of charges, 10J, 10K, and 10L, present on features, 4F, 4G, and 4H. A structure 12 comprising negatively charged labels 13B is brought in proximity to surface 1A. The negatively charged labels experience an electrostatic repulsive force from the negatively charged surface. Since the density of negative charges is higher on surface than on features, the electrostatic repulsive force between the labels and surface is substantially higher than any electrostatic repulsive force between labels and features. Structure 12 is placed is proximity to surface 1. An application of negative charge to surface 12 generates a repulsive force between surface 12 and labels 13B. This repulsive force is less than or equal to the repulsive force between labels 13B and surface 1. Accordingly, labels 13B are not attached to surface 1. Furthermore, the repulsive force between labels 13B and structure 12 is substantially higher than the repulsive force between labels 13B and features, 4E, 4F, 4G, and 4H. Accordingly, labels are attached only to features and not to surface 1A. After the labels are attached to features, structure 12 is moved away from surface 1A. Finally, the negative charges on surface 1A are discharged.

FIG. 3D illustrates a method to attach a positively charged label to a non-conducting feature on a conducting surface using electrostatic force, in accordance with the invention. A surface 1A comprises four non-conducting features, 4E, 4F, 4G, and 4H, having different shapes, sizes, and material properties. The surface 1A is positively charged. In some embodiments, charging of surface 1A is by performed by electrical conduction. Electrical conduction involves bringing a charged conducting structure in contact with surface 1A. In other embodiments, charging of surface 1A is performed by electrostatic induction. Induction involves bringing a charged structure close to surface 1A, wherein the charged structure does not physically make contact with surface 1A. In some embodiments, charging of surface 1A is performed with friction, by physically interacting the surface with another material, so that surface 1A is positively charged. Features, 4E, 4F, 4G, and 4H, are non-conducting, so they do not possess free electrons. Nevertheless, the electron clouds of atoms in the features are displaced when the features are charged. The charge density of positive charges on surface 1A is a lot higher when compared to charge density of positive charges on features 4E, 4F, 4G, and 4H. The distribution of charges on surface 1A is seen to be substantially denser than the distribution of charges 10M present on feature 4E. Similarly, the distribution of charges on surface 1A is substantially denser than the distribution of charges, 10N, 10P, and 10Q, present on features, 4F, 4G, and 4H. A structure 12 comprising positively charged labels 13A is brought in proximity to surface 1A. The positively charged labels experience an electrostatic repulsive force from the positively charged surface. Since the density of positive charges is higher on surface than on features, the electrostatic repulsive force between the labels and surface is substantially higher than any electrostatic repulsive force between labels and features. Structure 12 is placed is proximity to surface 1. An application of positive charge to surface 12 generates a repulsive force between surface 12 and labels 13A. This repulsive force is less than or equal to the repulsive force between labels 13A and surface 1. Accordingly, labels 13A are not attached to surface 1. Furthermore, the repulsive force between labels 13A and structure 12 is substantially higher than the repulsive force between labels 13A and features, 4E, 4F, 4G, and 4H. Accordingly, labels are attached only to features and not to surface 1A. After the labels are attached to features, structure 12 is moved away from surface 1A. Finally, the positive charges on surface 1A are discharged.

FIG. 3E illustrates a method to attach a positively charged label to a conducting feature on a non-conducting surface using electrostatic force, in accordance with the invention. A surface 1B comprises four conducting features, 4A, 4B, 4C, and 4D, having different shapes, sizes, and material properties. The features, 4A, 4B, 4C, and 4D, are negatively charged. In some embodiments, charging of features, 4A, 4B, 4C, and 4D, is performed by electrostatic induction. Induction involves bringing a charged structure close to surface 1B, wherein the charged structure does not physically make contact with surface 1B. The surface 1B is not negatively charged since it is non-conducting. Accordingly, the density of charges on features, 4A, 4B, 4C, and 4D, is substantially higher than the density of charges on surface 1B. The distribution of charges 10A present on feature 4A is seen to be substantially denser than the distribution of charges on surface 1B. Similarly, the distribution of charges, 10B, 10C, and 10D, present on features, 4B, 4C, and 4D, is seen to be substantially denser than the distribution of charges on surface 1B. A structure 12 comprising positively charged labels 13A is brought in proximity to surface 1B. The positively charged labels experience an electrostatic attractive force from the negatively charged features. Since the density of negative charges is higher on features than on surface, the electrostatic force between the labels and features is substantially higher than the electrostatic force between labels and surface. The electrostatic force between a label and a feature is directly proportional to the product of the charges in the label and the feature and inversely proportional to the square of the distance between the label and the feature. A predetermined distance between structure 12 and surface 1B allows one or more labels to experience an electrostatic force large enough to detach from structure 12 and attach to feature 4A. Similarly, other labels originally attached to structure 12 detach from structure 12 and attach features 4B, 4C, and 4D due to the electrostatic force between the label and the features. The electrostatic force between a label and a point on surface 1B is not large enough for the label to detach from structure 12. Accordingly, labels are attached only to features and not to surface 1B.

FIG. 3F illustrates a method to attach a negatively charged label to a conducting feature on a non-conducting surface using electrostatic force, in accordance with the invention. A surface 1B comprises four conducting features, 4A, 4B, 4C, and 4D, having different shapes, sizes, and material properties. The features, 4A, 4B, 4C, and 4D, are positively charged. In some embodiments, charging of features, 4A, 4B, 4C, and 4D, is performed by electrostatic induction. Induction involves bringing a charged structure close to surface 1B, wherein the charged structure does not physically make contact with surface 1B. The surface 1B is not positively charged since it is non-conducting. Accordingly, the density of charges on features, 4A, 4B, 4C, and 4D, is substantially higher than the density of charges on surface 1B. The distribution of charges 10E present on feature 4A is seen to be substantially denser than the distribution of charges on surface 1B. Similarly, the distribution of charges, 10F, 10G, and 10H, present on features, 4B, 4C, and 4D, is seen to be substantially denser than the distribution of charges on surface 1B. A structure 12 comprising negatively charged labels 13B is brought in proximity to surface 1B. The negatively charged labels experience an electrostatic attractive force from the positively charged features. However, since the density of positive charges is higher on features than on surface, the electrostatic force between the labels and features is substantially higher than the electrostatic force between labels and surface. The electrostatic force between a label and a feature is directly proportional to the product of the charges in the label and the feature and inversely proportional to the square of the distance between the label and the feature. A predetermined distance between structure 12 and surface 1B allows one or more labels to experience an electrostatic force large enough to detach from structure 12 and attach to feature 4A. Similarly, other labels originally attached to structure 12 detach from structure 12 and attach features 4B, 4C, and 4D due to the electrostatic force between the label and the features. The electrostatic force between a label and a point on surface 1B is not large enough for the label to detach from structure 12. Accordingly, labels are attached only to features and not to surface 1B.

FIG. 3G illustrates a method to attach a negatively charged label to a non-conducting feature on a non-conducting surface using electrostatic force, in accordance with the invention. A surface 1B comprises four non-conducting features, 4E, 4F, 4G, and 4H, having different shapes, sizes, and material properties. The surface 1B is positively charged. Although surface 1 is non-conducting, charging surface 1B displaces the electron clouds of atoms in surface 1. Positive charging of topside of surface 1 displaces electron cloud of atoms in surface 1B away from the topside of surface 1. In some embodiments, charging of surface 1B is performed by electrostatic induction. Induction involves bringing a charged structure close to surface 1B, wherein the charged structure does not physically make contact with surface 1B. Features, 4E, 4F, 4G, and 4H, are also positively charged. Although features, 4E, 4F, 4G, and 4H, are non-conducting, charging of features displaces the electron clouds of atoms in features. Positive charging of features shifts electron clouds of atoms in features away from the topside of surface 1. The density of charges on features, 4E, 4F, 4G, and 4H, is substantially higher than the density of charges on surface 1B. The distribution of charges 10M present on feature 4E is seen to be substantially denser than the distribution of charges on surface 1B. Similarly, the distribution of charges, 10N, 10P, and 10Q, present on features, 4F, 4G, and 4H, is seen to be substantially denser than the distribution of charges on surface 1B. Charge density is proportional to surface curvature. Since features, 4E, 4F, 4G, and 4H, have substantially higher curvature than surface 1B, charge density of the features are higher than that of the surface. A structure 12 comprising negatively charged labels 13B is brought in proximity to surface 1B. The negatively charged labels experience an electrostatic attractive force from the positively charged features and the positively charged surface. However, since the density of positive charges is higher on features than on surface, the electrostatic force between the labels and features is substantially higher than the electrostatic force between labels and surface. The electrostatic force between a label and a feature is directly proportional to the product of the charges in the label and the feature and inversely proportional to the square of the distance between the label and the feature. A predetermined distance between structure 12 and surface 1B allows one or more labels to experience an electrostatic force large enough to detach from structure 12 and attach to feature 4A. Similarly, other labels originally attached to structure 12 detach from structure 12 and attach features 4B, 4C, and 4D due to the electrostatic force between the label and the features. The electrostatic force between a label and a point on surface 1B is not large enough for the label to detach from structure 12. Accordingly, labels are attached only to features and not to surface 1B.

FIG. 3H illustrates a method to attach a positively charged label to a non-conducting feature on a non-conducting surface using electrostatic force, in accordance with the invention. A surface 1B comprises four non-conducting features, 4E, 4F, 4G, and 4H, having different shapes, sizes, and material properties. The surface 1B is negatively charged. Although surface 1 is non-conducting, charging surface 1B displaces the electron clouds of atoms in surface 1. Negative charging of topside of surface 1 displaces electron cloud of atoms in surface 1B towards the topside of surface 1. In some embodiments, charging of surface 1B is performed by electrostatic induction. Induction involves bringing a charged structure close to surface 1B, wherein the charged structure does not physically make contact with surface 1B. Features, 4E, 4F, 4G, and 4H, are also negatively charged. Although features, 4E, 4F, 4G, and 4H, are non-conducting, charging of features displaces the electron clouds of atoms in features. Negative charging of features shifts electron clouds of atoms in features towards the topside of surface 1. The density of charges on features, 4E, 4F, 4G, and 4H, is substantially higher than the density of charges on surface 1B. The distribution of charges 10I present on feature 4E is seen to be substantially denser than the distribution of charges on surface 1B. Similarly, the distribution of charges, 10J, 10K, and 10L, present on features, 4F, 4G, and 4H, is seen to be substantially denser than the distribution of charges on surface 1B. Charge density is proportional to the surface curvature. Since features, 4E, 4F, 4G, and 4H, have substantially higher curvature than surface 1B, charge density of the features are higher than that of the surface. A structure 12 comprising positively charged labels 13B is brought in proximity to surface 1B. The positively charged labels experience an electrostatic attractive force from the negatively charged features and the negatively charged surface. However, since the density of negative charges is higher on features than on surface, the electrostatic force between the labels and features is substantially higher than the electrostatic force between labels and surface. The electrostatic force between a label and a feature is directly proportional to the product of the charges in the label and the feature and inversely proportional to the square of the distance between the label and the feature. A predetermined distance between structure 12 and surface 1B allows one or more labels to experience an electrostatic force large enough to detach from structure 12 and attach to feature 4A. Similarly, other labels originally attached to structure 12 detach from structure 12 and attach features 4B, 4C, and 4D due to the electrostatic force between the label and the features. The electrostatic force between a label and a point on surface 1B is not large enough for the label to detach from structure 12. Accordingly, labels are attached only to features and not to surface 1B.

FIG. 4 illustrates a method to attach a label to a feature on a surface 1 by immersing the surface in a medium 15 comprising the label, in accordance with the invention. Surface 1 comprises four features, 4A, 4B, 4C, and 4D, having different shapes, sizes, and material properties. Medium 15 comprises labels that are to be attached to the features on surface. The labels in the medium are targeted to attach to the features, but not to the surface. In some embodiments, labels are designed to attach to specific feature types. In some embodiments, medium 15 contains multiple label types that are designed to attach to multiple feature types. For example, labels may be designed to attach to a particular material type and not to other commonly found material types of features. In some embodiments, medium 15 comprises charged labels that are attached to features with electrostatic forces. In such embodiments, features are specifically targeted so that labels are attached only to features and not the surface. Targeting of features by charged labels could be performed using the differences in charge density between features and a surface. In some embodiments, labels are attached to features with a chemical bond. In some embodiments, features are targeted by labels due to their non-smooth structure when compared to surface 1. In such embodiments, labels are unable to attach to surface 1 since the smooth nature of surface 1 does not inhibit the flow of labels in medium, leading to a decreased probability of interaction between labels and surface. On the other hand, features, 4A, 4B, 4C, and 4D, inhibit the flow of labels in medium, leading to an increased probability of interaction between labels and features.

FIG. 5 illustrates a surface 1 having labeled features, in accordance with the invention. Surface 1 comprises four features, 4A, 4B, 4C, and 4D, having different shapes, sizes, and material properties. One or more labels 14A are attached to feature 4A. Similarly, one or more labels, 14B, 14C, and 14D, are attached to features 4B, 4C, and 4D. Labels are selectively attached to features, but not to surface 1.

FIG. 6A illustrates a method to detach a label from a feature on a surface using a negatively charged substrate, in accordance with the invention. In some embodiments, it may be desirable to detach labels from features after label radiation has been captured. Doing so will eliminate the possibility of labels to affect the functionality of an IC. In some embodiments, the impact of labels on the functionality of an IC is negligible when compared to the impact of features on the functionality of ICs. A negatively charged structure is in close proximity to surface 1. Surface 1 comprises four features, 4A, 4B, 4C, and 4D, having different shapes, sizes, and material properties. One or more labels 14A are attached to feature 4A. Similarly, one or more labels, 14B, 14C, and 14D, are attached to features 4B, 4C, and 4D. Labels are positively charged. An electrostatic force attracts the positively charged labels towards the negatively charged structure. The attractive electrostatic force is larger than the force between labels and features. Accordingly, labels are detached from features and are attached to substrate 15.

FIG. 6B illustrates a method to detach a label from a feature on a surface using a positively charged substrate, in accordance with the invention. In some embodiments, it may be desirable to detach labels from features after label radiation has been captured. Doing so will eliminate the possibility of labels to affect the functionality of an IC. In some embodiments, the impact of labels on the functionality of an IC is negligible when compared to the impact of features on the functionality of ICs. A positively charged structure is in close proximity to surface 1. Surface 1 comprises four features, 4A, 4B, 4C, and 4D, having different shapes, sizes, and material properties. One or more labels 14A are attached to feature 4A. Similarly, one or more labels, 14B, 14C, and 14D, are attached to features 4B, 4C, and 4D. Labels are negatively charged. An electrostatic force attracts the negatively charged labels towards the positively charged structure. The attractive electrostatic force is larger than the force between labels and features. Accordingly, labels are detached from features and are attached to substrate 15.

Figure 7:
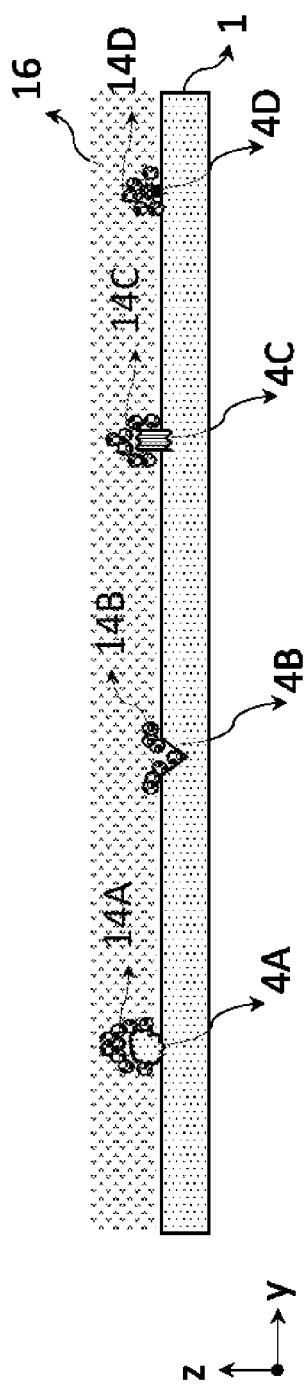
FIG. 7 illustrates a method to detach a label from a feature on a surface by immersing the surface in a medium, in accordance with the invention.

FIG. 7 illustrates a method to detach a label from a feature on a surface by immersing the surface in a medium, in accordance with the invention. In some embodiments, it may be desirable to detach labels from features after label radiation has been captured. Doing so will eliminate the possibility of labels to affect the functionality of an IC. In some embodiments, the impact of labels on the functionality of an IC is negligible when compared to the impact of features on the functionality of ICs. A surface 1 comprises features, 4A, 4B, 4C, and 4D, that are attached to labels, 14A, 14B, 14C, and 14D, respectively. The surface is immersed in a medium 16. The interaction of the medium with labels detaches the labels from features. In some embodiments, detaching a label from a feature involves breaking a chemical bond between the feature and the label. In some embodiments, medium 16 is a solvent for the labels. In other embodiments, medium 16 forms a chemical bond with labels.

Figure 8:
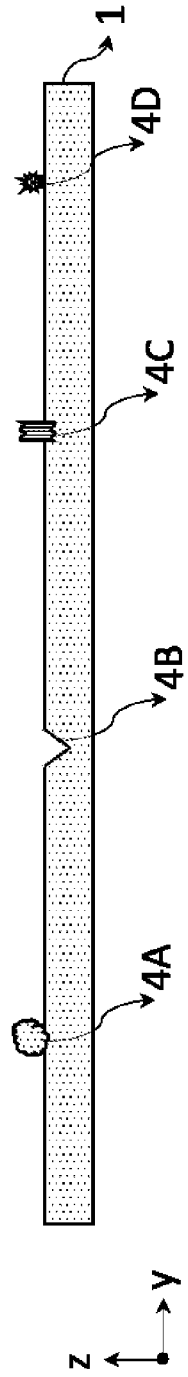
FIG. 8 illustrates a surface after labels are detached from features, in accordance with the invention.

FIG. 8 illustrates a surface after labels are detached from features, in accordance with the invention. In some embodiments, labels are detached with an electrostatic force. In other embodiments, labels are removed by immersing surface 1 in a medium to detach labels from features. After detachment of labels, surface 1 comprises features, 4A, 4B, 4C, and 4D without a substantial coating of labels.

FIG. 9 shows an exemplary flowchart to estimate feature properties using an image of label, in accordance with the invention. In block 17, labels are attached to features on a surface. The labels are selectively targeted to the features so that the labels attach only to the features and not to the surface. In some embodiments, labels are fluorescent markers. In other embodiments, labels are phosphorescent markers. In some embodiments, the wavelength of radiation absorbed by labels is shorter than the wavelength radiation emitted by the labels. In other embodiments, the wavelength of radiation absorbed by labels is longer than the wavelength radiation emitted by the labels. In such embodiments, the labels absorb multiple photons simultaneously. The wavelength of radiation emitted by labels is different from the wavelength of radiation absorbed by labels. This difference in wavelengths helps in separating label radiation from surface radiation and feature radiation. In some embodiments, labels are attached to features using an electrostatic force by charging both labels and features. Targeting of labels only to features may be accomplished by creating a difference in charge density between labels and a surface. In some embodiments, labels are attached to features by immersing the surface having the features in a medium containing the labels. In some embodiments, labels are attached to features with a chemical bond.

In block 18, an image of label is captured. An image of label is captured by a detector having one or more pixels. The detector detects label radiation originating from labels attached to features. The image of label does not have surface radiation and feature radiation. This is accomplished by using a filter that transmits label radiation, but does not transmit feature radiation and surface radiation. In some embodiments, the filter is an interference filter. In other embodiments, the filter is a dichroic beam splitter or a dichroic mirror. In some embodiments, the filter is an absorptive filter. In some embodiments, the detector is an image sensor having a plurality of pixels. The image sensor could be a complementary metal oxide semiconductor (CMOS) type imager or a charge coupled device type (CCD) imager. In some embodiments, the detector is a photomultiplier tube (PMT). In other embodiments, the detector is a photodiode such as an avalanche photodiode. In some embodiments, the image of label is formed by scanning a surface relative to the detector so that label radiation from multiple points on the surface is detected by the detector at different times. The data detected at different times are then stitched to form an image of label. In other embodiments, the detector captures label radiation from a wide region of surface. In such embodiments, label radiation from different surface regions are captured by different pixels of the detector.

In some embodiments, the detector comprises an image sensor and a micro-optic sensor layer for phase detection. The micro-optic sensor layer comprises a plurality of lenses implemented as a refractive optical element or a diffractive optical element. In some embodiments, each lens of the micro-optic sensor layer generates an image of the aperture of an imaging module on the pixels of image sensor. A finite number of pixels are allocated in image sensor for each lens on the micro-optic sensor layer. The pixels allocated for a lens of micro-optic sensor layer are located around the center of the optical axis of the lens. From the intensities of pixels allocated for the lens, the phase gradient of scattered radiation incident on the lens is determined. For example, if the pixel intensity corresponds to a focused spot in the center of the allocated pixels (on the optical axis of lens), then the scattered radiation can be estimated to have a zero phase gradient when it is incident on the surface of the lens. Alternatively, if the pixel intensity corresponds to a focused spot that is not at the center of the allocated pixels for the lens, then the scattered light can be estimated to have a linear phase gradient that is proportional to the distance between the focused spot and the center of allocated pixels. Accordingly, a phase gradient value can be estimated for each lens of the micro-optic sensor layer. A phase gradient profile for the surface of the micro-optic sensor layer can be estimated by combining phase gradients of a plurality of lenses in the micro-optic sensor layer using a stitching algorithm. The phase profile of scattered radiation, $P(x,y)$, is computed from the estimated phase gradient profile by calculating a two dimensional integration of the phase gradient profile. The intensity of scattered light, $I(x,y)$, is obtained from the pixel intensities detected by image sensor. The electromagnetic field of scattered light, $C(x,y)$, is calculated from the intensity and phase of scattered radiation as, $C(x,y)=\sqrt{I(x,y)}e^{(-iP(x,y))}$. The electromagnetic field $C(x,y)$ may then be propagated using computational propagation to bring different planes in focus. For example, $C(x,y)$ may be computationally propagated to bring a surface in focus, thereby generating a focused image of label. Alternatively, $C(x,y)$ may be propagated to bring a plane above or below a surface in focus, thereby generating a defocused image of label.

In some embodiments, computational propagation is performed in the spatial frequency domain by first computing spatial frequencies of electromagnetic field using a transformation. Then, a propagation transfer function is computed and multiplied with spatial frequencies of the electromagnetic field. In some embodiments, computing spatial frequencies of an electromagnetic field involves the calculation of $\tilde{C}(k_x,k_y)=F\{C(x,y)\}$, where $C(x,y)$ is electromagnetic field, F refers to Fourier transform, and $\tilde{C}(k_x,k_y)$ is the spatial frequency of $C(x,y)$. Propagation transfer function, $\tilde{H}(k_x,k_y)$, is computed as $$\tilde{H}(k_x, k_y) = e^{\left(i\Delta z\sqrt{(k^2-k_x^2-k_y^2)}\right)},$$

where $k=2\pi n/\lambda$, n is refractive index, $\lambda$ is the wavelength of the electromagnetic beam, and $\Delta z$ is the distance through which the electromagnetic field is propagated. The electromagnetic field after propagation is computed as, $F^{-1}\{\tilde{C}(k_x,k_y)\tilde{H}(k_x,k_y)\}$, where $F^{-1}$ refers to inverse Fourier transformation. In other embodiments, computational propagation of an electromagnetic field is performed by first computing an impulse response or point spread function of propagation, and then computing a convolution of the electromagnetic field with the impulse response. The impulse response of propagation is calculated as $$F^{-1}\left\{e^{\left(i\Delta z\sqrt{(k^2-k_x^2-k_y^2)}\right)}\right\}.$$

In some embodiments, $\Delta z$ is calculated as the product of the square of the magnification of imaging module with the distance in z through which the field needs to be propagated in the object space of imaging module. In some embodiments, computational propagation may be achieved by using digital refocusing algorithms that operate in the geometrical optics regime by rearranging pixel values to compute different focal planes.

In block 19, label pixels are located from the captured image of label. One or more images of label are processed to separate label pixels from background pixels. The label pixels are located by searching for pixels, in image of label, that possess substantially different pixel values when compared to other pixels in local neighborhood. In some embodiments, a focused image of label is used for detecting label pixels. This is because of high intensity values of label pixels in focused images of label. Label pixels may be classified from their background pixels using an intensity threshold value. To minimize false positives, threshold values are designed to be higher than background pixel values. The value of a threshold may be adaptively chosen depending on pixel intensities in local neighborhood. For example, threshold value in a region with high background is higher than the threshold value in a region with lower background. In some embodiments, one or more focused labels may be modeled and the model shape may be correlated with image of label. Such a correlation operation creates correlation peaks at the position of labels. Correlation peaks may then be distinguished from their background using an intensity threshold value. A label pixel region, comprising a predetermined number of pixels that are surrounding the detected label pixels, is segmented for estimating feature properties.

In block 20, properties of features are estimated. Properties of features include information on position, size, shape, and material composition. The position is estimated by localizing the position of label pixels. In some embodiments, the position of a feature is estimated as the peak, centroid, or the midpoint of label pixels. In some embodiments, position is estimated by fitting the label pixels with a model of an image of label. Fitting may be done by first interpolating label pixels and the model, and by shifting the model relative to the interpolated label pixels. Each shift is followed by computing the difference between the shifted model and the interpolated label pixels at each shift value. The position of shift value generating the least difference is estimated as the position of feature. The size of a feature is estimated from the size of label pixel region in the x and y dimensions. Images of label focused at multiple planes could be used to estimate the size of feature along the z dimension. In some embodiments, the brightness of label pixels is used to estimate the number of labels attached to feature. The number of labels attached to a feature is related to the size of the feature. In some embodiments, number of labels attached to the feature is related to the charge density of the feature. The charge density of feature is related to material properties of feature such as conductance. The shape of a feature may be estimated from multiple focused and defocused images of label. Defocused images of label are useful to estimate feature shape because label radiation spans over more number of pixels in a defocused image than in the case of a focused image. In some embodiments, shape of a feature is estimated by comparing defocused images of label with previously known models of defocused images of label. The shape corresponding to the model having the closest match with image of label is estimated as the shape of the feature. Comparison between image of label and a model may be done by computing the difference between a model and the image of label.

FIG. 10 shows an exemplary flowchart to estimate feature properties using an image of label and an image of feature, in accordance with the invention. In block 50, labels are attached to features on a surface. The labels are selectively targeted to the features so that the labels attach only to the features and not to the surface. In some embodiments, labels are fluorescent markers. In other embodiments, labels are phosphorescent markers. In some embodiments, the wavelength of radiation absorbed by labels is shorter than the wavelength radiation emitted by the labels. In other embodiments, the wavelength of radiation absorbed by labels is longer than the wavelength radiation emitted by the labels. In such embodiments, the labels absorb multiple photons simultaneously. The wavelength of radiation emitted by labels is different from the wavelength of radiation absorbed by labels. This difference in wavelength helps in separating label radiation from surface radiation and feature radiation. In some embodiments, labels are attached to features using an electrostatic force by charging both labels and features. Targeting of labels only to features may be accomplished by creating a difference in charge density between labels and the surface. In some embodiments, labels are attached to features by immersing the surface having the features in a medium containing the labels. In some embodiments, labels are attached to features with a chemical bond.

In block 51, an image of label is captured. An image of label is captured by a detector having one or more pixels. The detector detects label radiation originating from labels attached to features. The image of label does not have surface radiation and feature radiation. This is accomplished by using a filter that transmits label radiation, but does not transmit feature radiation and surface radiation. In some embodiments, the filter is an interference filter. In other embodiments, the filter is a dichroic beam splitter or a dichroic mirror. In some embodiments, the filter is an absorptive filter. In some embodiments, the detector is an image sensor having a plurality of pixels. The image sensor could be a complementary metal oxide semiconductor (CMOS) type imager or a charge coupled device type (CCD) imager. In some embodiments, the detector is a photomultiplier tube (PMT). In other embodiments, the detector is a photodiode such as an avalanche photodiode. In some embodiments, the image of label is formed by scanning a surface relative to the detector so that label radiation from multiple points on the surface is detected by the detector at different times. The data detected at different times are then stitched to form an image of label. In other embodiments, the detector captures label radiation from a wide region of surface. In such embodiments, label radiation from different surface regions are captured by different pixels of the detector.

In some embodiments, the detector comprises an image sensor and a micro-optic sensor layer for phase detection. The micro-optic sensor layer comprises a plurality of lenses implemented as a refractive optical element or a diffractive optical element. In some embodiments, each lens of the micro-optic sensor layer generates an image of the aperture of an imaging module on the pixels of image sensor. A finite number of pixels are allocated in image sensor for each lens on the micro-optic sensor layer. The pixels allocated for a lens of micro-optic sensor layer are located around the center of the optical axis of the lens. From the intensities of pixels allocated for the lens, the phase gradient of scattered radiation incident on the lens is determined. For example, if the pixel intensity corresponds to a focused spot in the center of the allocated pixels (on the optical axis of lens), then the scattered radiation can be estimated to have a zero phase gradient when it is incident on the surface of the lens. Alternatively, if the pixel intensity corresponds to a focused spot that is not at the center of the allocated pixels for the lens, then the scattered light can be estimated to have a linear phase gradient that is proportional to the distance between the focused spot and the center of allocated pixels. Accordingly, a phase gradient value can be estimated for each lens of the micro-optic sensor layer. A phase gradient profile for the surface of the micro-optic sensor layer can be estimated by combining phase gradients of a plurality of lenses in the micro-optic sensor layer using a stitching algorithm. The phase profile of scattered radiation, $P(x,y)$, is computed from the estimated phase gradient profile by calculating a two dimensional integration of the phase gradient profile. The intensity of scattered light, $I(x,y)$, is obtained from the pixel intensities detected by image sensor. The electromagnetic field of scattered light, $C(x,y)$, is calculated from the intensity and phase of scattered radiation as, $C(x,y)=\sqrt{I(x,y)}e^{(-iP(x,y))}$. The electromagnetic field $C(x,y)$ may then be propagated using computational propagation to bring different planes in focus. For example, $C(x,y)$ may be computationally propagated to bring a surface in focus, thereby generating a focused image of label. Alternatively, $C(x,y)$ may be propagated to bring a plane above or below a surface in focus, thereby generating a defocused image of label.

In some embodiments, computational propagation is performed in the spatial frequency domain by first computing spatial frequencies of electromagnetic field using a transformation. Then, a propagation transfer function is computed and multiplied with spatial frequencies of the electromagnetic field. In some embodiments, computing spatial frequencies of an electromagnetic field involves the calculation of $\tilde{C}(k_x,k_y)=F\{C(x,y)\}$, where $C(x,y)$ is electromagnetic field, F refers to Fourier transform, and $\tilde{C}(k_x,k_y)$ is the spatial frequency of $C(x,y)$. Propagation transfer function, $\tilde{H}(k_x,k_y)$, is computed as $$\tilde{H}(k_x, k_y) = e^{\left(i\Delta z\sqrt{(k^2-k_x^2-k_y^2)}\right)},$$

where $k=2\pi n/\lambda$, n is refractive index, $\lambda$ is the wavelength of the electromagnetic beam, and $\Delta z$ is the distance through which the electromagnetic field is propagated. The electromagnetic field after propagation is computed as, $F^{-1}\{\tilde{C}(k_x,k_y)\tilde{H}(k_x,k_y)\}$, where $F^{-1}$ refers to inverse Fourier transformation. In other embodiments, computational propagation of an electromagnetic field is performed by first computing an impulse response or point spread function of propagation, and then computing a convolution of the electromagnetic field with the impulse response. The impulse response of propagation is calculated as $$F^{-1}\left\{e^{\left(i\Delta z\sqrt{(k^2-k_x^2-k_y^2)}\right)}\right\}.$$

In some embodiments, $\Delta z$ is calculated as the product of the square of the magnification of imaging module with the distance in z through which the field needs to be propagated in the object space of imaging module. In some embodiments, computational propagation may be achieved by using digital refocusing algorithms that operate in the geometrical optics regime by rearranging pixel values to compute different focal planes.

In block 52, label pixels are located from the captured image of label. One or more images of label are processed to separate label pixels from background pixels. The label pixels are located by searching for pixels, in image of label, that possess substantially different pixel values when compared to other pixels in local neighborhood. In some embodiments, a focused image of label is used for detecting label pixels. This is because of high intensity values of label pixels in focused images of label. Label pixels may be classified from their background pixels using an intensity threshold value. To minimize false positives, threshold values are designed to be higher than background pixel values. The value of a threshold may be adaptively chosen depending on pixel intensities in local neighborhood. For example, threshold value in a region with high background is higher than the threshold value in a region with lower background. In some embodiments, one or more focused labels may be modeled and the model shape may be correlated with image of label. Such a correlation operation creates correlation peaks at the position of labels. Correlation peaks may then be distinguished from their background using an intensity threshold value. A label pixel region, comprising a predetermined number of pixels that are surrounding the detected label pixels, is segmented for estimating feature properties.

In block 53, an image of feature is captured. An image of feature is captured by a detector having one or more pixels. The detector detects feature radiation originating from features and surface radiation originating from surface. The detector capturing image of feature does not detect label radiation. This is accomplished by using a filter that transmits label radiation but reflects feature radiation and surface radiation. In some embodiments, the filter is a dichroic beam splitter or a dichroic mirror. In some embodiments, the detector is an image sensor having a plurality of pixels. The image sensor could be a complementary metal oxide semiconductor (CMOS) type imager or a charge coupled device type (CCD) imager. In some embodiments, the detector is a photomultiplier tube (PMT). In other embodiments, the detector is a photodiode such as an avalanche photodiode. In some embodiments, the image of feature is formed by scanning a surface relative to the detector so that feature radiation and surface radiation from multiple points on the surface is detected by the detector at different times. The data detected at different times are then stitched to form an image of feature. In other embodiments, the detector captures feature radiation and surface radiation from a wide region of surface. In such embodiments, feature radiation and surface radiation from different surface regions are captured by different pixels of the detector.

In some embodiments, the detector comprises an image sensor and a micro-optic sensor layer for phase detection. An electromagnetic field is computed from the intensity and phase of feature radiation and surface radiation. The electromagnetic field may then be propagated using computational propagation to bring different planes in focus. For example, may be computationally propagated to bring a surface in focus, thereby generating a focused image of features. Alternatively, the electromagnetic field may be propagated to bring a plane above or below a surface in focus, thereby generating a defocused image of feature.

In block 54, feature pixels are located from the captured image of feature. One or more images of feature are processed to separate feature pixels from background pixels. The feature pixels are located by searching for pixels, in image of feature, that possess substantially different pixel values when compared to other pixels in local neighborhood. In some embodiments, a focused image of feature is used for detecting feature pixels. This is because of high intensity values of feature pixels in focused images of feature. Feature pixels may be classified from their background pixels using an intensity threshold value. To minimize false positives, threshold values are designed to be higher than background pixel values. The value of a threshold may be adaptively chosen depending on pixel intensities in local neighborhood. For example, threshold value in a region with high background is higher than the threshold value in a region with lower background. In some embodiments, one or more focused features may be modeled and the model shape may be correlated with image of feature. Such a correlation operation creates correlation peaks at the position of features. Correlation peaks may then be distinguished from their background using an intensity threshold value. A feature pixel region, comprising a predetermined number of pixels that are surrounding the detected feature pixels, is segmented for estimating feature properties.

In block 55, properties of features are estimated from label pixel region and feature pixel region. In this block, information from feature pixels are combined with information from label pixels to detect features and to estimate feature properties. In some embodiments, feature pixels are combined with label pixels as a weighted average to facilitate detection of feature. Properties of features include information on position, size, shape, and material composition. The position of a feature is estimated by localizing the position of label pixels and feature pixels. In some embodiments, the position of a feature is estimated as the peak, centroid, or the midpoint of label pixels and feature pixels. In some embodiments, position is estimated by fitting the label pixels with a model of an image of label, and by fitting the feature pixels with a model of an image of feature. Fitting of label pixels may be done by first interpolating label pixels and a model, and by shifting the model relative to the interpolated label pixels. Each shift is followed by computing the difference between the shifted model and the interpolated label pixels at each shift value. The position of shift value generating the least difference is estimated as the position of feature computed from label pixels. Similarly, fitting of feature pixels may be done by first interpolating feature pixels and a model, and by shifting the model relative to the interpolated feature pixels. Each shift is followed by computing the difference between the shifted model and the interpolated feature pixels at each shift value. The position of shift value generating the least difference is estimated as the position of feature computed from feature pixels. The position of feature computed from label pixels and the position of feature computed from feature pixels are then combined as a weighted average to calculate the combined estimate of feature position. The weights in the weighted average may be determined based on the precision of an estimate. For example, if the position of feature computed from label pixels has a higher precision (lower uncertainty) than the position of feature computed from feature pixels, then the position of feature computed from label pixels is assigned a higher weight than the position of feature computed from feature pixels.

The size of a feature is estimated from the size of label pixel region and the size of feature pixel region in the x and y dimensions. Images of label and images of feature focused at multiple planes could be used to estimate the size of feature along the z dimension. In some embodiments, the brightness of label pixels is used to estimate the number of labels attached to feature. The number of labels attached to a feature is related to the size of the feature. In some embodiments, number of labels attached to the feature is related to the charge density of the feature. The charge density of feature is related to material properties of feature such as conductance. In some embodiments, the brightness of pixels in feature image is used to estimate the size of the feature. This is because intensity of feature radiation increases with feature size. The size of feature computed from label pixels and the size of feature computed from feature pixels are then combined as a weighted average to calculate the combined estimate of feature size. The weights in the weighted average may be determined based on the precision of an estimate. For example, if the size of feature computed from label pixels has a higher precision (lower uncertainty) than the size of feature computed from feature pixels, then the size of feature computed from label pixels is assigned a higher weight than the size of feature computed from feature pixels.

The shape of a feature may be estimated from multiple focused and defocused images of label and images of feature. Defocused images of label and defocused images of feature are useful to estimate feature shape because label and feature radiation spans over more number of pixels in a defocused image than in the case of a focused image. In some embodiments, shape of a feature is estimated by comparing defocused images of label and images of feature with previously known models of defocused images of label and images of feature, respectively. The shape corresponding to the label model having the closest match with image of label is estimated as the shape of the feature. Similarly, the shape corresponding to the feature model having the closest match with image of feature is estimated as the shape of the feature. Comparison between image of label and a model may be done by computing the difference between a model and the image of label. Similarly, comparison between image of feature and a model may be done by computing the difference between a model and the image of feature. The shape of feature computed from label pixels and the shape of feature computed from feature pixels are then combined as a weighted average to calculate the combined estimate of feature shape. The weights in the weighted average may be determined based on the precision of an estimate. For example, if the shape of feature computed from label pixels has a higher precision (lower uncertainty) than the shape of feature computed from feature pixels, then the shape of feature computed from label pixels is assigned a higher weight than the shape of feature computed from feature pixels.

In some embodiments, surface properties such a surface roughness are estimated from the image of feature. The image of feature detects surface radiation and feature radiation. While image regions corresponding to feature radiation are typically sparsely located, image regions corresponding to surface radiation are distributed throughout the image of feature, as a substantially uniform background within a local neighborhood of pixels. The pixel values corresponding to this background is related to the roughness of surface. For example, background pixel values increase as the magnitude of surface roughness increases. Therefore, an estimate of surface roughness may be computed from background pixel values of image of feature.

FIG. 11 shows an exemplary flowchart to attach and detach labels from features on surface, in accordance with the invention. In block 21, labels are attached to features on a surface. The labels are selectively targeted to the features so that the labels attach only to the features and not to the surface. In some embodiments, labels are fluorescent markers. In other embodiments, labels are phosphorescent markers. In some embodiments, the wavelength of radiation absorbed by labels is shorter than the wavelength radiation emitted by the labels. In other embodiments, the wavelength of radiation absorbed by labels is longer than the wavelength radiation emitted by the labels. In such embodiments, the labels absorb multiple photons simultaneously. The wavelength of radiation emitted by labels is different from the wavelength of radiation absorbed by labels. This difference in wavelength helps in separating label radiation from surface radiation and feature radiation. In some embodiments, labels are attached to features using an electrostatic force by charging both labels and features. Targeting of labels only to features may be accomplished by creating a difference in charge density between labels and the surface. In some embodiments, labels are attached to features by immersing the surface having the features in a medium containing the labels. In some embodiments, labels are attached to features with a chemical bond. In block 45, an image of label is captured. An image of label is captured by a detector having one or more pixels. The detector detects label radiation originating from labels attached to features. The image of label does not have surface radiation and feature radiation. This is accomplished by using a filter that transmits label radiation, but does not transmit feature radiation and surface radiation. In some embodiments, the filter is an interference filter. In other embodiments, the filter is a dichroic beam splitter or a dichroic mirror. In some embodiments, the filter is an absorptive filter. In some embodiments, the detector is an image sensor having a plurality of pixels. The image sensor could be a complementary metal oxide semiconductor (CMOS) type imager or a charge coupled device type (CCD) imager. In some embodiments, the detector is a photomultiplier tube (PMT). In other embodiments, the detector is a photodiode such as an avalanche photodiode. In some embodiments, the image of label is formed by scanning a surface relative to the detector so that label radiation from multiple points on the surface is detected by the detector at different times. The data detected at different times are then stitched to form an image of label. In other embodiments, the detector captures label radiation from a wide region of surface. In such embodiments, label radiation from different surface regions are captured by different pixels of the detector. In some embodiments, the detector comprises an image sensor and a micro-optic sensor layer for phase detection. In block 46, labels are removed or detached from features on surface. In some embodiments, labels are removed with an electrostatic force. In other embodiments, labels are removed by immersing the surface in a solution. Removing labels from features will eliminate the possibility of labels to affect the functionality of an IC. In some embodiments, the impact of labels on the functionality of an IC is negligible when compared to the impact of features on the functionality of ICs.

Figure 12:
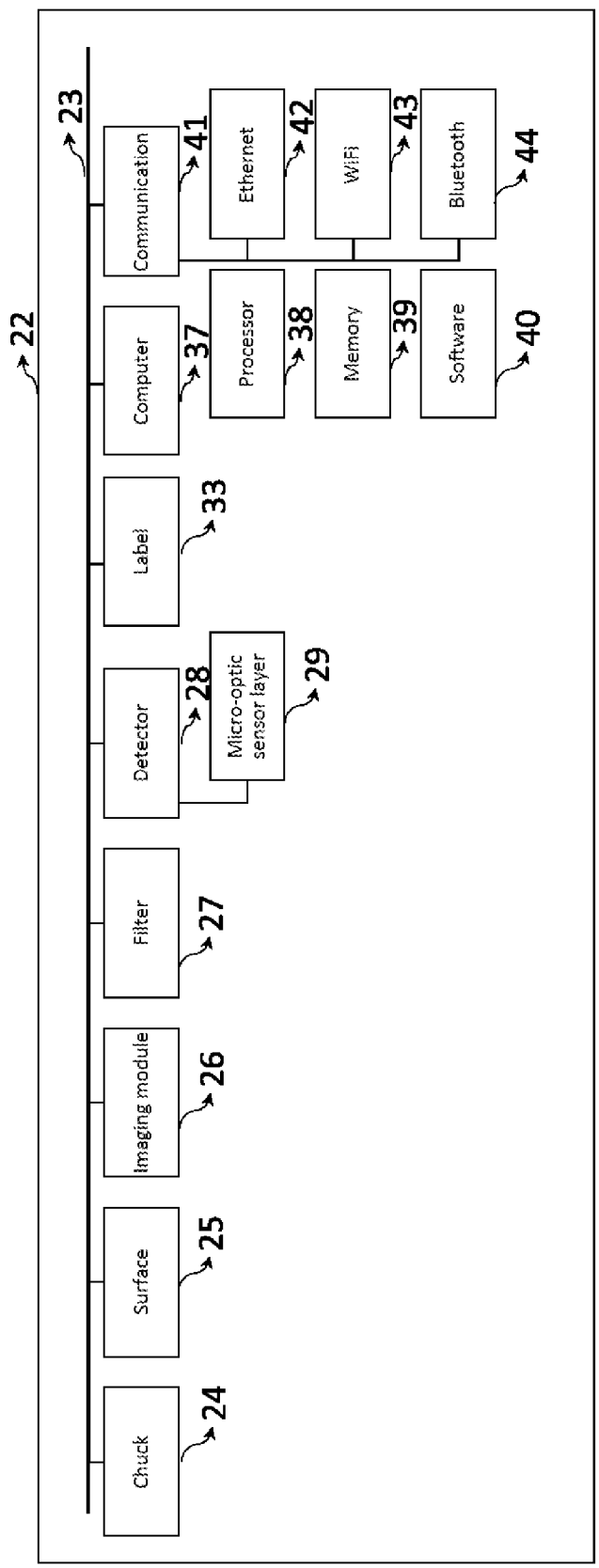
FIG. 12 illustrates a system for labeled wafer inspection, in accordance with the invention.

FIG. 12 illustrates a system for labeled wafer inspection, in accordance with the invention. A bus 23 connects various blocks of system 22, namely chuck 24, surface 25, imaging module 26, filter 27, detector 28, label 33, computer 37, and communication 41. Data and control signals are carried by bus 23. Chuck 24 includes an edge handling system that holds the edge of surface, vacuum system that holds the back side of surface with vacuum suction, gas vents, and support structures used to hold surface 25 flat. Surface 25 comprises the region to be inspected by system 22. Surface 25 may be flat, curved due to gravity induced sag, or deformed due to coatings. Imaging module 26 forms an image of label and an image of feature. Filter 27 separates label radiation from feature radiation and surface radiation. In some embodiments, detector 28 comprises a detectors to capture label radiation. In some embodiments, detector 28 also comprises a second detector to capture feature and surface radiation. The images captured by detector 28 are transferred through bus 23 to computer 37. In some embodiments, detector 28 may include a micro-optic sensor layer 29 to facilitate phase detection. Detector 28 receives control information to adjust parameters such as exposure time and gain from computer 37 through bus 23. Computer 37 includes a processor 38, memory 39, and software 40. Software 40 processes image data from detector 28 to compute a number of entities, including: intensity and phase profiles of electromagnetic field; computational propagation to compute image of label and image of feature; stitching of data to form image of label and image of feature; locating label pixels; locating feature pixels; feature model; label model; feature properties such as position, size, shape, and type; and surface properties. Software 40 generates control information and sends them through bus 23 to chuck 24, surface 25, imaging module 26, and detector 28. Computer 37 connects to communication block 41 for communicating data and control information through bus 23. Communication block 41 includes Ethernet 42, WiFi 43, and Bluetooth 44.

It will be recognized by those skilled in the art that various modifications may be made to the illustrated and other embodiments of the invention described above, without departing from the broad inventive scope thereof. It will be understood therefore that the invention is not limited to the particular embodiments or arrangements disclosed, but is rather intended to cover any changes, adaptations or modifications which are within the scope and spirit of the invention as defined by the appended claims.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described above, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A wafer inspection system for detecting a feature located on a surface, comprising:
    a label attached to said feature, wherein said feature comprises one or more material types;
    an electromagnetic radiation incident on said label, said feature, and said surface to generate a label radiation from said label, a feature radiation from said feature, and a surface radiation from said surface;
    an imaging module positioned to collect said label radiation, said feature radiation, and said surface radiation;
    a filter positioned to receive radiation from said imaging module, wherein said filter separates said label radiation from said feature radiation and said surface radiation;
    a detector having one or more pixels disposed to capture the separated label radiation for generating an image of label; and
    a processor configured to locate label pixels corresponding to said label radiation by searching for pixels, in said image of label, that possess substantially different pixel values when compared to other pixels in local neighborhood,
    whereby said feature is located by detecting said label.

2. The system of claim 1, wherein said label is attached to said feature with an electrostatic force.

3. The system of claim 2, wherein said feature is a defect or an abnormality present on said surface.

4. The system of claim 1, wherein said label is attached to said feature by immersing said surface in a medium comprising said label.

5. The system of claim 1, wherein said label is attached to said feature by a chemical bond.

6. The system of claim 1, wherein said filter is a dichroic filter used as beam splitter to separate label radiation from feature and surface radiation.

7. The system of claim 1, further comprising a second detector having one or more pixels disposed to capture feature radiation for generating an image of feature.

8. The system of claim 7, wherein said processor is further configured to
    locate feature pixels corresponding to said feature radiation by searching for pixels, in said image of feature, that possess substantially different pixel values when compared to other pixels in local neighborhood; and
    combine information from said feature pixels with information from said label pixels to detect said feature.

9. The system of claim 7, further comprising a spatial filter positioned between said filter and the second detector, wherein the spatial filter modulates the feature radiation and the surface radiation in order to maximize feature sensitivity.

10. The system of claim 1, further comprising a micro-optic sensor layer for detecting phase of radiation.

11. The system of claim 1, further comprising means for varying the optical path length between imaging module and detector.

12. The system of claim 1, wherein said detector captures an image of a substantial area of said surface.

13. The system of claim 1, wherein said image of label is generated by combining detector signals captured at multiple spatial locations on said surface by scanning said surface relative to said detector.

14. The system of claim 1, wherein label radiation has a substantially different wavelength than feature radiation and surface radiation.

15. The system of claim 1, wherein said electromagnetic radiation undergoes specular reflection on said surface to generate specular radiation, with said specular radiation prevented from being detected by said detector.

16. The system of claim 1, wherein said label is a fluorescent marker or a phosphorescent marker.

17. A wafer inspection method for detecting a feature located on a surface, comprising:
   attaching a label to said feature, wherein said feature comprises one or more material types;
   generating a label radiation from said label, a feature radiation from said feature, and a surface radiation from said surface;
   collecting said label radiation, said feature radiation, and said surface radiation;
   separating said label radiation from said feature radiation and said surface radiation;
   capturing the separated label radiation for generating an image of label, with said image of label having one or more pixels; and
   locating label pixels corresponding to said label radiation by searching for pixels, in said image of label, that possess substantially different pixel values when compared to other pixels in local neighborhood,
   whereby said feature is located by detecting said label.

18. The method of claim 17, further comprising detaching of said label from said feature with an electrostatic force or by breaking a chemical bond.

19. The method of claim 17, further comprising detaching of said label from said feature by immersing said surface in a medium.

20. The method of claim 17, further comprising estimation of properties of said feature using said label pixels, wherein the feature properties include position and size of said feature.

* * * * *